(12) United States Patent
Swinkels et al.

(10) Patent No.: US 6,265,186 B1
(45) Date of Patent: Jul. 24, 2001

(54) YEAST CELLS COMPRISING AT LEAST TWO COPIES OF A DESIRED GENE INTEGRATED INTO THE CHROMOSOMAL GENOME AT MORE THAN ONE NON-RIBOSOMAL RNA ENCODING DOMAIN, PARTICULARLY WITH KLUYVEROMYCES

(75) Inventors: Bart Willem Swinkels, Delft; Albert Johannes Joseph Van Ooijen, Voorburg; Adriana Cornelia Maria Noordermeer-Van Der Haak, Wateringen, all of (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 09/402,817
(22) PCT Filed: Apr. 14, 1998
(86) PCT No.: PCT/EP98/02261
§ 371 Date: Dec. 10, 1999
§ 102(e) Date: Dec. 10, 1999
(87) PCT Pub. No.: WO98/46774
PCT Pub. Date: Oct. 22, 1998

(30) Foreign Application Priority Data

Apr. 11, 1997 (EP) .................................. 97201053

(51) Int. Cl.[7] .............................. C12P 21/06; C12N 1/16; C12N 15/63
(52) U.S. Cl. ..................... 435/69.1; 435/254.2; 435/483
(58) Field of Search .............................. 435/69.1, 254 A, 435/483

(56) References Cited

U.S. PATENT DOCUMENTS 4,745,062  5/1988  Guerineau et al. .................. 435/209

FOREIGN PATENT DOCUMENTS 0 068 740 A2  1/1983  (EP).
0 077 689 A2  4/1983  (EP).
0 088 632 A2  9/1983  (EP).

(List continued on next page.)

OTHER PUBLICATIONS

R.J.M. Bergkamp et al., Current Genetics, vol. 21, 1992, pp. 365–370.
Wery J et al., Gene (Amsterdam), 184(1), 1997, pp. 89–97.
Mochizukin D et al., Journal of Fermentation and Bioengineering, 77(5), 1994, pp. 468–473.
Yip C W et al., World Journal of Microbiology & Biotechnology, 13(1), 1997, pp. 103–117.
Marie–Therese Le Dall et al., Current Genetics, vol. 26, No. 1, 1994, pp. 38–44.
A. Sakai et al., Bio/Technology, vol. 9, Dec. 1991, pp. 1382–1385.
A. Plessis et al., Gene, vol. 134, 1993, pp. 41–50.
J. A. Van Den Berg et al., Bio/Technology, vol. 8, No. 2, Feb. 1990, pp. 135–139.

(List continued on next page.)

*Primary Examiner*—Robert A. Schwartzman
*Assistant Examiner*—Katharine F Davis
(74) *Attorney, Agent, or Firm*—McDonnell Boehnen Hulbert & Berghoff

(57) ABSTRACT

The present invention provides for a yeast cell comprising at least two copies of a desired gene integrated into its chromosomal genome, wherein said genome comprises at least two DNA domains suitable for integration of one or more copies of said desired gene, which domains share substantial sequence homology and are non-ribosomal RNA encoding DNA domains, and wherein at least two of said substantially homologous non-ribosomal RNA encoding DNA domains have at least one copy of the said desired gene integrated. The invention also provides methods for making yeast cells according to the invention, as well as the use thereof for making a protein, a peptide or a metabolite.

45 Claims, 11 Drawing Sheets

FOREIGN PATENT DOCUMENTS

| | | |
|---|---|---|
| 0 123 544 A2 | 10/1984 | (EP). |
| 0 127 304 A1 | 12/1984 | (EP). |
| 0 139 383 A1 | 5/1985 | (EP). |
| 0 163 491 A1 | 12/1985 | (EP). |
| 0 164 556 A2 | 12/1985 | (EP). |
| 0 301 669 A1 | 2/1989 | (EP). |
| 0 301 670 A1 | 2/1989 | (EP). |
| 0 394 538 A1 | 11/1990 | (EP). |
| 0 213 593 B1 | 4/1991 | (EP). |
| 0 123 811 B1 | 6/1991 | (EP). |
| 0 183 070 B1 | 10/1991 | (EP). |
| 0 531 187 A1 | 3/1993 | (EP). |
| 0 537 456 A1 | 4/1993 | (EP). |
| 0 635 574 A1 | 1/1995 | (EP). |
| 0 707 068 A1 | 4/1996 | (EP). |
| 0 748 872 A1 | 12/1996 | (EP). |
| 0 481 008 B1 | 11/1997 | (EP). |
| 2 059 280 | 11/1994 | (ES). |
| 9 001 159 | 12/1991 | (NL). |
| WO 83/04050 A1 | 11/1983 | (WO). |
| WO 90/05787 A1 | 5/1990 | (WO). |
| WO 90/14423 A1 | 11/1990 | (WO). |
| WO 93/03159 A1 | 2/1993 | (WO). |
| WO 94/01569 A1 | 1/1994 | (WO). |
| WO 94/01570 A1 | 1/1994 | (WO). |
| WO 94/03618 A1 | 2/1994 | (WO). |
| WO 94/13821 A1 | 6/1994 | (WO). |
| WO 95/23857 A1 | 9/1995 | (WO). |
| WO 95/25799 A1 | 9/1995 | (WO). |
| WO 97/23633 A1 | 7/1997 | (WO). |

OTHER PUBLICATIONS

Miller, 1972, Experiments in molecular Genetics—Cold Spring Harbor Laboratory Press, 352–355.
Schwartz and Cantor, 1984, Cell, 37:(67 et seq.).
Struhl et al., Poc. Natl. Acad. Sci. USA, 1979, 76:1035–1039.
Dickson and Markin, 1978, Cell, 15:123–130.
Ito et al., 1983, J. Bact., 153:163–168.
Breunig et al., 1984, Nucleic Acids Res., 12:2327–2341.
Alani et al., 1987, Genetics 116:541–545.
Das & Hollenberg, 1982, Current Genet., 6:123–128.
Sambrook et al., Molecular Cloning: a Laboratory Manual, 2nd Edition, 1989, Cold Spring Harbor Laboratory Press.

YEAST CELLS COMPRISING AT LEAST TWO COPIES OF A DESIRED GENE INTEGRATED INTO THE CHROMOSOMAL GENOME AT MORE THAN ONE NON-RIBOSOMAL RNA ENCODING DOMAIN, PARTICULARLY WITH KLUYVEROMYCES

TECHNICAL FIELD

The present invention is in the field of genetic modification of yeast using recombinant DNA techniques. The invention is more particularly concerned with the production of yeast cells incorporating into the genome multiple copies of a desired gene, as well as yeast cells so obtained. The invention is further concerned with the production of proteins, peptides and metabolites, by growing yeast cells so obtained under conditions conducive to the expression of the said desired gene, whereby the production of the protein, peptide or metabolite is achieved.

BACKGROUND ART

A known method of obtaining yeast strains harbouring multiple copies of a desired gene is in the use of multicopy plasmids. Plasmids, however have several disadvantages: (i) the expression level expressed in terms of the ratio of desired protein produced to copy number of the desired gene is generally lower for plasmids than for integrated copies of the desired gene; thus, plasmids impose a bigger metabolic burden to the cell than integrated copies, which may result in a penalty in terms of biomass accumulation; (ii) plasmids are prone to structural instability which may lead to loss of the desired gene from the plasmid or to a partial protein product; (iii) plasmids may give rise to segregational instability leading to plasmid loss. The latter especially occurs if high level expression is desired which imposes a strong metabolic burden to the cell.

To overcome mitotic instability associated with plasmids, integration of multiple copies of a desired gene has met with some success in yeast. Multiple copies of desired genes have been integrated at a single integration site in the genome, mostly in the ribosomal DNA of the yeast genome. Multicopy integration at a single locus is almost invariably achieved by the integration of multiple copies in tandem in the yeast genome; this easily leads to instability due to out-recombination of copies of the construct as a consequence of the presence of direct repeats flanking the construct containing the desired gene. The more copies that are found in tandem, the easier it leads to excision by out-recombination of single copies, thereby decreasing protein production levels to an unpredictable, but lower, level.

To overcome some of the instability, a system was devised to obtain integration of high copy numbers in the ribosomal DNA by using a deficient selection marker, for example wherein a weak promoter is cloned in front of the selection marker (EP 0 481 008). A first disadvantage is the need of selection markers in the production strain. Dominant antibiotic-resistance markers are less desirable from a regulatory standpoint whereas on the other hand auxotrophic markers are often not useful because they require mutant recipient host strains. Moreover, the presence of selection markers may also add to an unwanted complexity of the fermentation. Secondly, the ribosomal RNA encoding DNA locus is found in a nuclear organelle called the nucleolus, which is not an ideal location for obtaining optimal expression of a protein-encoding gene, as protein encoding genes are RNA-polymerase-II transcribed genes.

It is an object of the invention to provide for yeast cells having multiple copies of a desired gene integrated into the genome without some or all of the problems encountered with yeast cells known in the prior art.

SUMMARY OF THE INVENTION

The present invention provides for the first time, as isolated clone, a yeast cell comprising at least two copies of a desired gene integrated into its chromosomal genome, wherein said chromosomal genome comprises at least two DNA domains suitable for integration of one or more copies of said desired gene, which domains share substantial sequence homology and are non-ribosomal RNA encoding DNA domains, and wherein at least two of said substantially homologous non-ribosomal RNA encoding DNA domains incorporate at least one copy of the said desired gene.

Preferred according to the invention are yeast cells, wherein at least two of said substantially homologous non-ribosomal RNA encoding DNA domains suitable for integration of one or more copies of said desired gene incorporate two or more copies of the said desired gene, more preferably, wherein each substantially homologous non-ribosomal RNA encoding DNA domain suitable for integration of one or more copies of said desired gene incorporates an identical number of copies of the said desired gene. Said substantially homologous non-ribosomal RNA encoding DNA domains suitable for integration of one or more copies of said desired gene may be substantial duplicates of each other, preferably allelic forms of each other. A preferred yeast cell according to the invention is one which is a Kluyveromyces yeast cell, such as a K. lactis or K. fragilis.

Preferred according to the invention are desired genes which are recombinant genes, meaning that at least some part of the desired gene has been manipulated using modern genetic engineering techniques. According to one embodiment the desired gene is a yeast gene. According to another embodiment the desired gene is a non-yeast gene. In any event, "gene" means a gene capable of being expressed when present in the yeast host of choice. The present invention is exemplified by a yeast gene coding for β-galactosidase (LAC4, from K. lactis) and a non-yeast gene coding for chymosin. The LAC4 gene is an intracellular gene, the chymosin gene actually codes for a preproprotein which is secreted as prochymosin, which can be autocatalytically activated to form the mature protein product chymosin. A gene coding for chymosin is herein understood to include all forms of DNA sequences which encode polypeptide that can be processed or matured into a protein with chymosin activity and thus specifically include cDNAs encoding prepro- and prochymosin. The desired gene may be a recombinant gene comprising a transcription promoter region, and optionally further a transcription termination region, functional in the said yeast cell, wherein at least one of said regions, or both are not naturally linked to the open reading frame coding for a protein or peptide. It will be clear that desired genes having regulatory regions that are by their nature already functional in the yeast cell of choice can be expressed in yeast cells in their native state.

According to one preferred embodiment the number of non-ribosomal RNA encoding DNA domains suitable for integration of one or more copies of said desired gene is two and the number of copies of said desired gene per domain is three, preferably at least three, more preferably at least four, more preferably at least five.

According to one embodiment the yeast cell according to the invention is a marker gene free yeast cell.

According to another embodiment a yeast cell is provided wherein said substantially homologous non-ribosomal RNA encoding DNA domains are LAC4 alleles.

The invention further provides for a method of producing a protein or peptide, comprising the step of growing a yeast cell according to any one of the preceding claims under conditions conducive to the production of said protein or peptide. Optionally, the said method further comprises the step of recovering the protein, peptide or metabolite from the cells and/or from the culture medium.

According to yet another embodiment a method is provided of obtaining a yeast cell capable of producing a desired protein or peptide comprising the steps of: (a) transforming a yeast cell having a genome which comprises at least two DNA domains suitable for integration of one or more copies of a desired gene, which domains share substantial sequence homology and are non-ribosomal RNA encoding DNA domains, with a DNA molecule comprising a desired gene which codes for the said protein or peptide, or a precursor thereof, and a region of homology with a said domain; (b) selecting or screening for cells having obtained at least one copy of the said desired gene integrated into at least one of said non-ribosomal RNA encoding DNA domains suitable for integration of one or more copies of a desired gene; and, (c) propagating the cells obtained in (b) and screening or selecting for cells having obtained at least one copy of the said desired gene integrated into at least two of said non-ribosomal RNA encoding DNA domains.

Preferred according to the invention is a method comprising in addition to step (a), (b) and (c) the step of: (d) propagating the cells obtained in (c) and screening or selecting for cells having obtained at least one copy of the said desired gene integrated into an additional copy of said non-ribosomal RNA encoding DNA domains.

Still further preferred according to the invention is a method comprising in addition to step (a), (b) (c) and (d) the step of: (e) repeating step (d) until each copy of said non-ribosomal RNA encoding DNA domains has obtained at least one integrated copy of the said desired gene.

Still further preferred according to the invention are methods wherein, a bidirectional selectable marker is used in the transformation of the yeast cells in step (a), and wherein removal of the selectable marker is effected prior to step (c). Preferably the bidirectional selectable marker is a dominant marker, more preferably an acetamidase gene. In yet another preferred method according to the invention, step (a) is repeated at least once, subsequent to the removal of the bidirectional selectable marker.

In another preferred embodiment according to the invention provides a method of obtaining a yeast cell capable of producing a desired protein or peptide comprising the steps of: (a) transforming a yeast cell having a genome which comprises at least two DNA domains suitable for integration of one or more copies of a desired gene, which domains share substantial sequence homology and are non-ribosomal RNA encoding DNA domains, with a DNA molecule comprising a desired gene which codes for the said protein or peptide, or a precursor thereof, and a region of homology with a said domain; (b) selecting or screening for cells having obtained at least one copy of the said desired gene integrated into at least one of said non-ribosomal RNA encoding DNA domains suitable for integration of one or more copies of a desired gene; (c) transforming a cell obtained in (b) with a second DNA molecule comprising a selectable marker gene, and a region of homology with a said domain; (d) selecting or screening for cells having obtained at least one copy of the said selectable marker gene integrated into one of said non-ribosomal RNA encoding DNA domains without one or more copies of the desired gene; and, (e) propagating the cells obtained in (d) and screening or selecting for cells having lost the selectable marker gene and having obtained at least one copy of the said desired gene integrated into at least two of said non-ribosomal RNA encoding DNA domains. Preferably, the selectable marker gene is a bidirectional marker gene, more preferably a dominant bidirectional marker gene, more preferably an acetamidase gene.

According to yet another embodiment a method is provided for obtaining a yeast cell capable of producing a desired protein or peptide, wherein said method comprises the steps of: (a) obtaining a transformed yeast cell with at least one copy of a desired gene integrated in one of its chromosomes, wherein the desired gene is flanked by direct repeats; (b) isolating single colonies from the progeny of the cell obtained in (a); (c) screening for single colony isolates having cells which have obtained at least one additional tandemly integrated copy of the desired gene, and, optionally; (d) repeating steps (a) to (c) on the cells obtained in (c) until a desired number of tandemly repeated copies of the desired gene is obtained. Preferred according to the invention is a method wherein the transformed yeast cell is a yeast cell having a genome which comprises at least two DNA domains suitable for integration of one or more copies of a desired gene, which domains share substantial sequence homology and are non-ribosomal RNA encoding DNA domains, and wherein the desired gene is integrated into at least one copy of said DNA domain, and wherein the method further comprises the steps of: (e) propagating the cells obtained in (c) or (d) and screening or selecting for cells having obtained copies of said desired gene integrated into at least two of said non-ribosomal RNA encoding DNA domains, and, optionally; and, (f) repeating the propagation and screening or selecting of (e) on the cells obtained in (e) until a desired number of said non-ribosomal RNA encoding DNA domains has obtained integrated copies of said desired gene.

The invention further provides a yeast cell of the genus Kluyveromyces which is non-haploid for at least one domain other than a ribosomal RNA-encoding DNA locus, preferably a *Kluyveromyces lactis* cell. According to another embodiment, the yeast cell is non-haploid for the LAC4 locus. Preferably, the yeast cell according incorporates in each allele of the said non-haploid locus one or more copies of a desired gene. More preferably the yeast cell incorporates the same number of copies of the said desired gene in each allele.

The invention further provides a method for making a protein, a peptide or a metabolite in yeast cells, wherein a yeast cell of the genus Kluyveromyces which is non-haploid for at least one non-ribosomal RNA-encoding DNA domain, preferably a *Kluyveromyces lactis* cell, is grown under conditions giving rise to the production of the said protein, peptide or metabolite.

The invention also provides for the use of a bidirectional marker gene for the selection of putative gene convertants of non-haploid yeast cells.

The invention also provides for the a Kluyveromyces yeast cell having at least 3 copies of a gene encoding lactase, or a derivative thereof, incorporated into its chromosomal genome, i.e. regardless of the chromosomal integration site(s). Likewise, the invention provides for the first time a Kluyveromyces yeast cell having at least 3 copies of a gene encoding chymosin, or a precursor or derivative thereof, incorporated into its chromosomal genome, regardless of the chromosomal integration site(s).

The invention further provides for a method of obtaining a yeast cell comprising at least two copies of a desired gene integrated into its chromosomal genome, wherein said genome comprises at least two DNA domains suitable for integration of one or more copies of said desired gene, which domains share substantial sequence homology and are non-ribosomal RNA-encoding DNA domains, and wherein each said substantially homologous non-ribosomal RNA-encoding DNA domain incorporates the same number of copies of the said desired gene, comprising the steps of
(1) selecting a yeast cell comprising at least one copy of a desired gene integrated into its genome, wherein said genome comprises at least two DNA domains suitable for integration of one or more copies of said desired gene, which domains share substantial sequence homology and are non-ribosomal RNA encoding DNA domains, and wherein at least one of said substantially homologous non-ribosomal RNA-encoding DNA domain incorporates a copy of the said desired gene, and wherein at least one of said domains incorporates less copies than at least one other domain in said cell;
(2) propagating said cell to obtain progeny cells, and
(3) identifying among said progeny a cell comprising at least two copies of a desired gene integrated into its genome, wherein said genome comprises at least two DNA domains suitable for integration of one or more copies of said desired gene, which domains share substantial sequence homology and are non-ribosomal RNA-encoding DNA domains, and wherein each said substantially homologous non-ribosomal RNA-encoding DNA domain incorporates an identical number of copies of the said desired gene.

The invention further provides a method of obtaining a yeast cell comprising an increased number of copies of a desired gene integrated into its genome, wherein said genome comprises at least two DNA domains suitable for integration of one or more copies of said desired gene, which domains share substantial sequence homology and are non-ribosomal RNA-encoding DNA domains, comprising the steps of:
(1) selecting a yeast cell comprising at least one copy of a desired gene integrated into its chromosomal genome, wherein said chromosomal genome comprises at least two DNA domains suitable for integration of one or more copies of said desired gene, which domains share substantial sequence homology and are non-ribosomal RNA-encoding DNA domains, and wherein at least one of said substantially homologous non-ribosomal RNA-encoding DNA domain incorporates a copy of the said desired gene, and wherein at least one of said domains incorporates less copies than at least one other domain in said cell;
(2) propagating said cell to obtain progeny cells, and
(3) identifying among said progeny cells a cell comprising at least two copies of a desired gene integrated into its chromosomal genome, wherein said genome comprises at least two DNA domains suitable for integration of one or more copies of said desired gene, which domains share substantial sequence homology and are non-ribosomal RNA-encoding DNA domains.

The invention further provides for a method of obtaining a yeast cell comprising at least two copies of a desired gene integrated into its chromosomal genome, wherein said chromosomal genome comprises at least two DNA domains suitable for integration of one or more copies of said desired gene, which domains share substantial sequence homology and are non-ribosomal RNA-encoding DNA domains, and wherein at least two of said substantially homologous non-ribosomal RNA-encoding DNA domains incorporate at least one copy of the said desired gene, comprising the steps of:
(1) transforming yeast cells with a DNA molecule comprising (a) a desired gene, (b) a region of homology with one of said domains in the genome, and (c) a bidirectional selection marker for selecting transformed cells;
(2) selecting transformed cells on the basis of the presence of the marker, and
(3) propagating transformed cells which have the DNA molecule integrated into a said domain, under counter-selective pressure favouring the loss of the bidirectional marker,
(4) transforming marker⁻ progeny cells of cells propagated in step (3) still incorporating one or more copies of the desired gene with a DNA molecule comprising (a) a bidirectional marker and (b) a region of homology with a said domain, and (5) selecting cells having obtained the said bidirectional marker integrated into a said domain in such a way that one domain has at least a bidirectional marker and one other domain has one or more copies of the desired gene,
(6) propagating bidirectional-marker⁺ cells under counter-selective pressure favouring the loss of the bidirectional marker, and
(7) identifying among the bidirectional-marker⁻ progeny cells obtained in step (6) progeny cells having at least two domains, each incorporating one or more copies of the desired gene. According to a preferred embodiment, the cells obtained have the same number of copies of the desired gene in each of said domains.

DETAILED DESCRIPTION OF THE INVENTION

Figure 1:
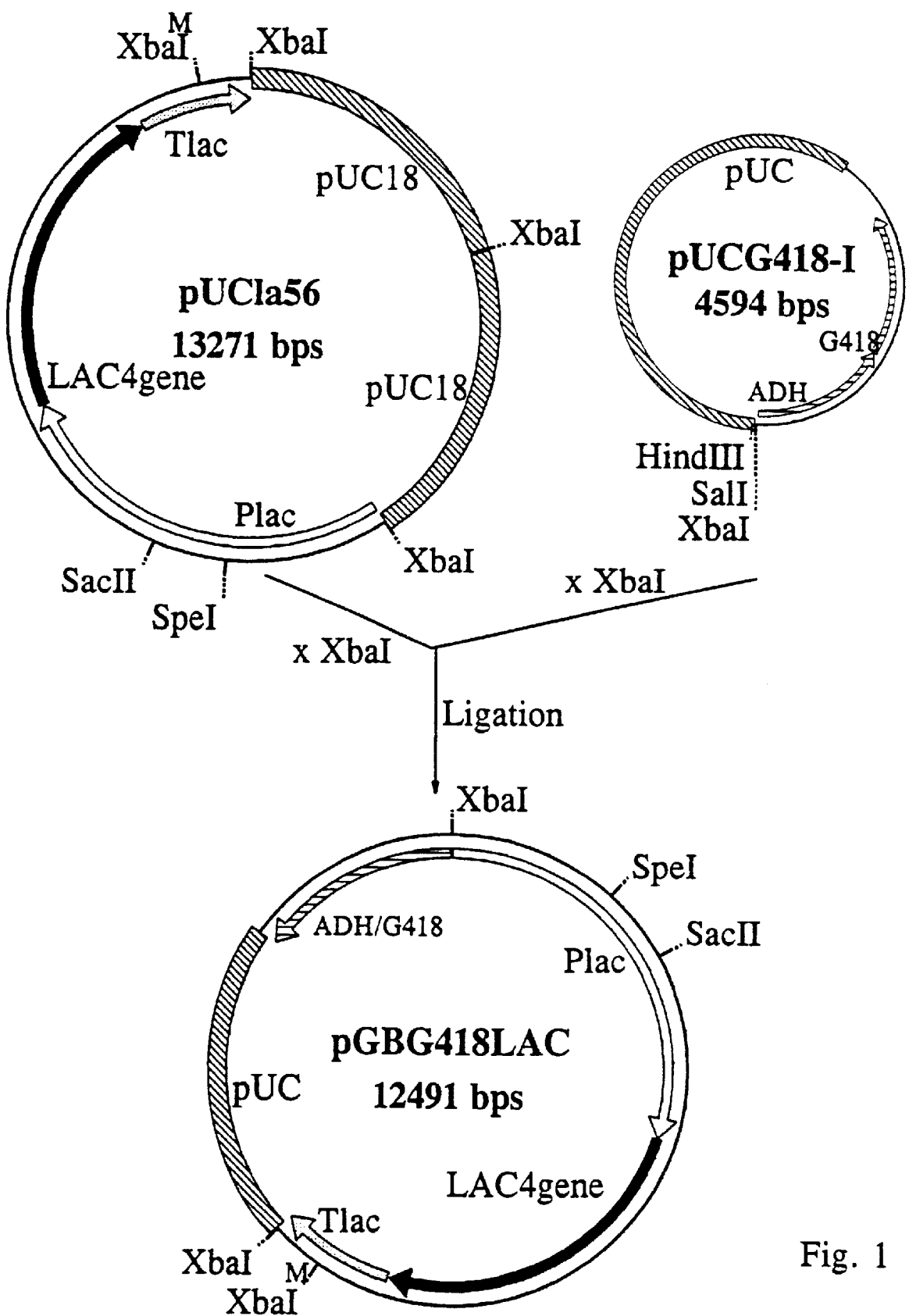
FIG. 1: Construction pathway of pGBG418LAC (M=methylated in *E. coli* JM109)

The yeast cells according to the invention comprise at least two copies of a desired gene integrated into its chromosomal genome, wherein said chromosomal genome comprises at least two DNA domains suitable for integration of one or more copies of said desired gene, which domains share substantial sequence homology and are non-ribosomal DNA domains, and wherein at least two of said substantially homologous non-ribosomal DNA domains incorporate a copy of the said desired gene. With chromosomal genome is meant the totality of chromosomes in the cell, artificial yeast chromosomes (YACs) included.

Preferably, each domain comprises more than two copies, still more preferably more than three copies, still more preferably between three and six copies of the desired gene. According to another preferred embodiment, each domain comprises the same number of copies of the desired gene.

The invention provides for the first time a method of obtaining yeast cells according to the invention. The invention is best understood by taking the following description as an example.

A yeast cell harbouring at least two substantially homologous domains suitable for integration of DNA, for example a strain which is diploid for a given locus, is transformed with an incoming DNA molecule which comprises (a) a desired gene, (b) a region of homology with the said domains in the genome, (c) optionally, a selection marker for detecting transformants. If a selection marker is being used, a bidirectional marker, such as amdS is preferred but not required, because after transformation it may be deleted from the genome (or inactivated) by counter-selection. In the alternative, the loss of the marker may be screened for (e.g. by replica plating), in which case counter-selection is not practised and the gene may be any gene suitable for use as a marker in a yeast cell. (In the case of amdS counter-selection may be done by using fluoracetamide as selective agent; details about the amdS gene and its use are provided in European patent application 0 635 574, published Jan. 25, 1991, in the name of Gist-Brocades N. V., the relevant parts of which are herein incorporated by reference).

Preferably, the (bidirectional) marker gene is flanked by direct repeats, allowing out-recombination from the genome at a later stage. In the examples herein, direct repeats are provided in the form of fragments comprising part of the LAC4 terminator region. Transformed cells are selected (or screened) first on the basis of the presence of the marker, and on the presence and the correct chromosomal location of the desired gene using routine genomic analysis techniques, such as gene amplification, Southern blots or TAFE (infra). Cells so selected are propagated, preferably under counter-selective pressure, and the deletion of the bidirectional marker is screened or selected for. Subsequently, marker-negative cells are transformed with a DNA molecule containing a (bidirectional) marker and a region of homology with the domains sufficient for recombinatorial integration into the genome. Transformed cells are selected or screened for the presence of the (bidirectional) marker, and among the marker$^+$ cells a clone is selected which has the (bidirectional) marker integrated in a non- or under-occupied domain; non- and under-occupied mean, domains which do not have a copy of the desired gene at all, or less copies than another homologous domain, respectively. This clone is propagated to allow for deletion of the (bidirectional) marker, preferably under counter-selective pressure. Progeny cells having lost the (bidirectional) marker (the frequency is between 1:100 and 1:5000) are analysed for genomic structure; of the marker$^-$ cells between about 1 and 20% is found to have, in exchange for the loss of the marker, a virtual copy of the first domain including a copy/copies of the desired genes integrated therein. This process, which can be selected for as described above, is hereinafter referred to as "gene conversion". Gene conversion is found to take place irrespective of the number of desired genes that are incorporated in the occupied domain. Thus, a cell comprising two copies of a desired gene integrated into its genome can give rise to four copy desired gene cell progeny by gene conversion, a three copy cell to six copy cell progeny, etc. The frequency of gene conversion is generally quite low; we have observed a frequency of about 1:15000 with the chymosin gene, but frequencies may vary with the nature of the desired gene.

The ability to screen for an increased copy number of the desired gene integrated into the chromosomal genome is important, since screening on increased copy numbers by determining protein or metabolite productivity is no longer feasible on lab-scale beyond a point where the contribution of productivity of each additional copy to the productivity levels off. It should be understood, that as the productivity determined at lab-scale levels off upon increasing the copy number beyond a certain point, still a major advantage may be seen in fermentations on an industrial scale.

The invention is exemplified in *Kluyveromyces lactis* as representative of yeast. It will be clear that the invention is equally well suitable for practising with other yeast species of the genus Kluyveromyces, such as *Kluyveromyces fragilis*, as well as with yeast belonging to other genera of the yeast kingdom, such as Saccharomyces, Schizosaccharomyces, Schwanniomyces, Yarrowia, Pichia, Hansenula, Candida, Phaffia, and the like. In principle any yeast species having two or more domains which share sequence homology for example by gene duplication or gene multiplication (also referred to as gene-amplification), as the case may be, and which are suitable for integration of a desired gene, such as a desired gene, can be used to obtain a strain having more than one copy integrated into the genome in more than one domain. According to one embodiment yeast strains are being used which are diploid or polyploid for a domain suitable for integrating a desired gene. Strains may be diploid or polyploid for a given domain, yet haploid, or x-ploid, for others; such strains are generally referred to as aneuploid. For ease of reference these will be referred to as hereinafter collectively as "non-haploid" species. An example of a European patent application describing the transformation of a non-haploid Saccharomyces species is EP 0 163 491. In the examples the HO locus is being used for integration of the lacZ gene in *Saccharomyces carlsbergensis*. Yeast cells having one or more copies of a desired gene integrated into more than one domain may be, in theory, directly selected from primary transformants disclosed in the examples of EP 0 163 491, using the method according to the invention. In order to identify cells having at least one copy in more than one domain it is preferred to propagate the primary transformants, remove the marker, retransform with bidirectional marker, select for transformants having the marker in the non-occupied domain, counter-select for cells having lost the marker and select among the marker cells those which are gene-convertants by analysing their genomes. Preferred starting strains are those having already more than one copy (tandemly) integrated into the first domain, because gene convertants resulting from such strains have their desired gene copy doubled.

In the examples herein, use is made of *K. lactis* CBS 685.97 which is diploid for the LAC4 locus and for several other loci. However, *K. lactis* CBS 685.97 does have a mating type and is thus not a true diploid cell.

It will be clear, that the invention is by no means limited to a given locus in the *K. lactis* chromosomal genome, or any other locus in another yeast species, for that matter. The invention is not limited to loci in the strict meaning of that expression. Classically the expression "locus" refers to a physical location of a "gene" on the chromosome. It should be clear that integration of one or more copies of a desired gene does not necessarily have to take place in or near a gene. Integration may equally well take place into some other form of genomic chromosomal DNA not being a gene, such as repetitive DNA, but other than ribosomal DNA repeats. For this reason the use of the expression "domain" is used for the purposes of this invention, rather than locus. It will be obvious that the domain according to the invention must be suitable for integration; by this is meant, that the integration must not negatively interfere with a desired function of said domain. For example if the domain is an active gene (a locus in fact) integration should not interfere with expression of that resident gene, if the expression of that gene is not to be negatively affected. If the functioning of the resident gene is not important, or even not desired, than integration may as well be in a domain within the gene, thereby impairing the genes functioning. It is emphasised, that chromosomal genome is intended to comprise the totality of chromosomes in any given yeast host, including any artificial chromosomes the yeast host may carry. Thus, the non-ribosomal RNA-encoding domains may be on the same chromosome (amplified) and/or on different chromosomes, and/or on yeast artificial chromosomes (YACs).

Although this situation may be less preferred, a domain may be suitable for integration even if it affects the functioning of a desired gene, provided that another copy not harbouring an integrated gene survives intact.

According to one embodiment a domain suitable for integration is a gene coding for an endogenous, undesirable protease activity. Deleting, or impairing the expression of such a gene, may result in higher protein recovery, to mention one example. An example of such a domain is Yeast Aspartyl protease (Yap3) EP 0 749 478 (published as WO 95/23857 on 8-09-1995).

According to another embodiment yeast cells may be obtained wherein a multiplicity of domains suitable for integration of one or more copies of a desired gene are incorporated into the chromosomal genome by transformation. For example a yeast cell may be obtained by integrating two or more copies of a DNA sequence into the genome, in a random fashion or otherwise this is not critical, to create "platforms" for subsequent targeted integration of one or more copies of a desired gene. These platforms are also envisaged as "domains suitable for integration" according to the invention.

Domains suitable for integration are to be non-ribosomal DNA loci. With ribosomal DNA locus is meant ribosomal RNA-encoding DNA locus, i.e. those regions in the genome comprising the ribosomal DNA repeats. Thus, not excluded for integration are the loci coding for ribosomal proteins, since the latter are clearly RNA-polymerase II transcribed loci.

The expression "suitable for integration" also implies that the length of the domain is such that recombination takes place with a reasonable frequency. It is generally known that the frequency of recombination of two (partially) homologous sequences increases with the length and degree of homology of the recombining DNA molecules. It is difficult to provide a strict minimum degree of homology or length of the homologous stretches, but those of skill are capable of practising the invention if the length of the homologous stretches is more than 100, preferably more than 300 bp. Stretches of homology of 2000 bp or more even further increase integration frequency by homologous recombination. There is no strict upper limit for the length of homology. Generally, the region of homology between the domains in the yeast cell genome may be as large as several thousand base pairs up to several hundreds of thousands of basepairs, this is not critical. It will be clear, that the region of homology in the transforming DNA may be much shorter than the length of the domains in the genome, since only a portion of the domain is needed for homologous recombination.

Best results are obtainable by using domains that are identical, or if not identical as homologous as possible. The fact that the invention works with allelic variants, which are not supposed to be identical, indicates that identity of the domains is no requirement.

Without wishing to be confined by theory, the identity, or homology, of the domains suitable for integration is thought to be preferable for two reasons:

(1) to promote recombination, and integration, of the incoming DNA molecules (comprising the desired gene) in more than one domain, on the basis of the same or very similar stretch of homology; these events are independent;

(2) to obtain "equalisation" of two homologous domains by a process which is hereinafter referred to as "gene conversion". The process by which this so-called gene conversion takes place is not elucidated as yet, but this is of no concern, as knowledge of its mechanism is not crucial for practising the invention.

The process of gene conversion, the use of which forms part of this invention, is manifested by the occurrence, in a small subpopulation of the entire population of cells, of domains which have acquired the same or similar structure as homologous domain. Thus, as illustrated by the present examples, a population of cells having one domain harbouring one copy of the desired gene and one (homologous) domain harbouring two copies of the desired gene counts (among its progeny cells) cells with one copy in both domains, as well as cell having two copies of the desired gene in both domains. As soon as the number of copies is equal in each of the homologous domains the situation is more stable than when the copies are unevenly distributed among the domains according to the invention. The copy number, however, tends to decrease nevertheless, although in the case of lactase, the productivity of the protein, peptide or metabolite is stable under industrial fermentation conditions for at least 50 generations. Similar experiments with cells harbouring up to 15 domains, have led to cells having an equal number copies (one or more) in each of the 15 domains. There appears to be a strong correlation between copy number and gene expression, as measured by determining the amount of protein product produced, up to a certain number of copies. The correlation factor may depend from gene to gene, and appears to level off at increasing copy number. The advantage, as will be clear to a person skilled in the art, is that each extra copy contributes significantly to a higher expression level of the desired gene, and consequently with a minimal waste of metabolic energy for the host cell.

Additionally, the surprisingly high stability of copy numbers in the cell population, in the absence of any selective pressure, will make it clear that the cells according to the invention have a significant advantage when used in an industrial fermentation process. The advantages are already significant in a fed-batch fermentation on industrial scale, in a continuous process the advantages are presumably higher.

Accordingly, the cells according to the invention can advantageously be used to produce large amounts of valuable compounds, such as proteins, peptides and metabolites. In addition, or alternatively, the cells can advantageously be used to make metabolites which accumulate, or accumulate in greater quantities, as a result of higher copy numbers, and as a consequence higher expression levels, of the desired gene.

The meaning of the word gene for the purposes of this invention is to be taken in a broad sense. It refers to genomic DNA, as well as to copy DNA (cDNA), or wholly or partially synthetic DNA. A gene according to this invention refers to a DNA sequence, together with expression regulating sequences operable in the yeast of choice, which encodes a protein, i.e. a structural protein or an enzyme, of any size. Also peptides (smaller proteins), such as peptide hormones, are included. A gene may encode for a monocistronic or a polycistronic messenger RNA (mRNA), i.e. coding for two or more polypeptide chains, which may be the same or different, or an mRNA coding for a fusion peptide. The protein or peptide may be produced as a proprotein requiring further processing of the polypeptide chain to obtain the desired mature protein. A protein or peptide may be produced in the form of a prepro-protein or -peptide (as is the case with many eukaryotic proteins). The pre-part commonly refers to a leader peptide which is cleaved from the maturing protein or peptide during passage through the secretory pathway of the yeast cell.

The gene may be modified in its regulatory elements, i.e. a different promoter, terminator, and/or other regulatory elements acting in modulating expression of the gene. In addition, or alternatively, a modification may involve the coding sequence of the gene, including modifications which leave the amino acid sequence of the encoded protein, or its precursor form, as such unaltered as well as modification which change the amino acid sequence.

All these changes can be routinely made by those of skill in the art, and they do not depart from the gist of this invention.

A desired gene as used herein is not limited to any sort of protein or peptide it may encode. The desired gene may be of yeast origin or a "non-yeast" gene. Examples of yeast genes are those coding for enzymes involved in metabolic pathways of the yeast itself, such as carotenoid biosynthesis, xanthophyll synthesis, ergosterol synthesis, nucleotide synthesis, and the like. Over-expression of the yeasts metabolic pathway genes may serve to over-produce certain metabolite intermediates or end-products in the said pathways. Other desired yeast genes according to the invention are those encoding enzymes such as invertase, glucose oxidase, lactase, malo ethanolic enzyme, and the like. Also envisaged as desired genes according to the invention are genes coding for enzymes which fit in existing metabolic pathways, or extend metabolic pathways such as to enhance the metabolic repertoire of the yeast cell. Examples of metabolic pathway engineering are legio.

Desired non-yeast genes according to the invention may be derived from animals, plants, bacteria and fungi, or their viruses, and they may encode structural proteins, peptides, such as hormone peptides, or enzymes. The encoded proteins or peptides or enzymes may have industrial or medicinal applications. Examples of industrial enzymes are lipases (e.g. used in the detergent industry), proteases (used inter alia in the detergent industry, in brewing and the like), cell wall degrading enzymes (such as, cellulases, pectinases, $\beta$-1,3/4- and $\beta$-1,6-glucanases, rhamnoga-lacturonases, mannanases, xylanases, pullulanases, galactanases, esterases and the like, used in fruit processing wine making and the like or in feed), phytases, phospholipases, glycosidases (such as amylases, $\beta$-glucosidases, arabinofuranosidases, rhamnosidases, apiosidases and the like), dairy enzymes (e.g. chymosin). Proteins, polypeptides and/or enzymes with therapeutic, cosmetic or diagnostic applications include but are not limited to insulin, human serum albumin (HSA), tissue plasminogen activator (tPA), erythropoietin (EPO), tumor necrosis factors (TNF), growth factors (G-CSF, GM-CSF, M-CSF, PDGF, EGF, and the like), peptide hormones (e.g. calcitonin, somatomedin, growth hormones, follicle stimulating hormone (FSH) interleukins (IL-x), interferons (IFN-y), bacterial and viral antigens, vaccines, receptors and the like. Also included are genes coding for mutants or analogues of the said proteins.

The present invention is especially advantageous when the desired gene is a cluster of genes which genes code for enzymes that are involved in a biochemical pathway in the yeast cell of choice. A cluster of desired genes may be integrated into the yeast chromosomal genome exactly as described for an individual desired gene according to the invention; in that case the DNA molecule with which the yeast cell is transformed is a cluster of desired genes which code for a number of enzymes, (b) a region of homology with a said domain and (c) a marker gene functional in said yeast cell, whereupon cells are selected or screened for having obtained the cluster of genes integrated into the chromosomal non-ribosomal RNA-encoding DNA. In the alternative, the desired genes making up the cluster of genes are integrated one or two at a time; this can advantageously be done using a bidirectional marker gene which is deleted after each round of transformation. According to experience, upon retransforming cells, integration of the incoming DNA molecule takes place in the already occupied domain with a higher frequency, than in the non-occupied domain. Thus, a situation can be selected or screened for, wherein one domain eventually has all the genes in the gene cluster integrated, whereas the other domain(s) have none, or an incomplete set. Subsequently, the under-occupied domain of the strain having the complete cluster integrated in the other domain is provided with a marker and selection or screening takes place on gene conversion exactly as described for single desired genes, resulting in doubling (or multiplication if the ploidy for the domain is higher than two) of the entire cluster takes place. By these methods yeast strains having multiple copies of entire gene clusters are advantageously integrated into the chromosomal genome where they are stably maintained and expressed. As an example of a gene cluster one involved in carotenoid biosynthesis in the yeast *Phaffia rhodozyma* may be mentioned; the cluster comprises a gene coding for an enzyme having geranylgeranyl pyrophosphate synthase (crtE), phytoene synthase activity (crtB), phytoene desaturase activity (crtI) and lycopene cyclase activity (crtY); the cloning of these genes is described in PCT/EP96/05887, a copy of which is herein incorporated by reference. Since this application has not yet been published a copy of the text is filed with this application as Annex.

The above genes are merely mentioned for purposes of illustration, they in no way serve to limit the invention.

Genes according to the invention may be under the control of their own regulatory elements, as long as the regulatory elements are functional in the host cell. Preferably, the regulatory regions are optimised for use in a particular yeast species. According to one embodiment the desired gene is a recombinant gene comprising a transcription promoter region, and optionally further a transcription termination region, functional in the said yeast cell. Suitable transcription promoters for expression of non-yeast as well as yeast genes are glycolytic promoters, such as the phosphofructokinase (PPK), triose phosphate isomerase (TPI), glyceraldehyde-3-phosphate dehydrogenase (GAPDH), pyruvate kinase (PK), phosphoglycerate kinase (PGK) promoters; more details about such promoters may be found in (WO 93/03159). Other useful promoters are ribosomal protein encoding gene promoters, the lactase gene promoter (LAC4), alcohol dehydrogenase promoter (ADH1, ADH4, and the like), enolase (ENO), the acid phosphatase promoter (PHO5). Also hybrid promoters may be considered. The choice of the promoter is not critical and depends on the desired gene, the purpose and the preference of the skilled person. The choice of the terminator is not critical, it may be from any yeast gene, although terminators may sometimes work if from a non-yeast, eukaryotic, gene.

As regards the number of domains suitable for integration of a desired gene, the invention is illustrated by two domains (two alleles of the LAC4 locus), but cells having 15 substantially homologous domains each incorporating one or more desired genes have been obtained via gene conversion. The number of copies of a desired gene which remain stable within a domain may depend from the identity of the desired gene. For the lactase gene, the situation where each of two domains incorporate three copies of the lactase gene, totalling 6 copies, appeared to be a very stable situation, giving a relative expression which is almost two and a half times higher than the two copy strain CBS 685.97, for more than 50 generations; compare LCT124 with CBS 685.97. The number of copies in any given domain appears to be limited by the fact, that integration tends to take place in a tandem-arrangement; for other desired genes than the LAC4 gene the number of copies per domain may be higher or lower. Whatever the number of copies per domain, a situation where each domain contains the same number of copies appears to much more stable than that wherein one domain contain less copies; the (3+3) situation is more favourable than the (2+4) situation; the latter tends to fall back to the (2+2) situation presumably due to gene conversion.

According to a preferred embodiment the yeast cells are marker gene free. This situation may be obtained by counter-selection for a bidirectional dominant selection marker, such as the acetamidase gene (amdS) from *Aspergillus nidulans*. This marker can be used to select for transformants having the gene by selecting with acetamide as sole carbon and/or nitrogen source, whereas counter-selection (a term reserved hereinafter for selection for the absence of the marker gene) can be done with, for example fluoracetamide. Other bidirectional dominant selection markers which work in yeasts can be used in an analogous fashion. The out-recombination of the bidirectional marker gene is facilitated by inserting the gene flanked by direct repeats on the incoming plasmid.

As disclosed in European patent application 0 635 574, the bidirectional marker is dominant in both directions, meaning that transformed cells of any genetic background can be selected for the presence of the marker (using acetamide as sole carbon and/or sole nitrogen source). Other bidirectional markers are URA3, LYS2, and the like, although the latter have the disadvantage that they are not "double dominant". To explain, selection for the presence of these type of markers in transformed cells requires an auxotrophic genetic background; in other words, these markers are recessive in one direction. In principle, this is no problem, since the media used during fermentations on an industrial scale are generally permissive for auxotrophs of the URA3 and LYS2 type (Alani et al., 1987, Genetics 116, 541–545). Counter-selection takes place by using selective agents consisting in non-toxic precursors of products which are toxic to the yeast cells; in the case of URA3 the precursor may for example be 5-fluoro-orotic acid. When the marker is present and expressed in the yeast, the harmless precursors are converted into the toxic product, thereby effectively selecting for marker loss among transformed cells.

The use of cells which are marker-free is more easily accepted by the regulatory authorities, and at the same time pose less burden to the energy balance of the yeast under industrial fermentation conditions.

The cells having an equal number of copies per substantially homologous domain are stable in their protein productivity for at least 50 generations, without the need for any form of selection pressure.

According to one embodiment a method for producing a protein or peptide is provided, comprising the step of growing a yeast cell according to the invention under conditions conducive to the production of said protein or peptide. Preferably such conditions are industrial fed batch conditions in large scale fermenters, such 100 m$^3$, more preferably more than 150 m$^3$, using cheap media for growth, such as molasses, or corn steep liquor. Also chemically defined media may be used in industrial scale fermentations, as the latter may provide considerable advantages in terms of process optimisation, herbicidal- and pesticidal residue control. The protein may be produced intracellularly or, extracellularly, and recovered from the cells or the culture medium, as the case may be. Means for recovery may include classical separation techniques well-known in the art, such as precipitation and/or centrifugation, column chromatography and the like. In case the product is a metabolite rather than a protein or peptide, similar considerations apply. Alternatively, the yeast cells may be used as such in a process (for example in brewing, baking, wine making, alcohol production, waste processing or the like) or as additive to feed or food, optionally after grinding (using for example ball mills to open up cells) and the like. None of the recovery techniques are critical to the instant invention.

Yeasts according to the invention may be propagated and sold for the sake of the yeast itself, such as for baking, brewing, wine making, to make cell walls and/or mannoproteins, or yeast extracts. Here, the yeast according to the invention may have added value due to their protein or metabolite content, which may be desirably increased or altered in composition according to the wishes of the user. The advantages of the strains are summarised below (non-limitative):

1. Stable integration;
2. Strong correlation between expression and gene copy;
3. Higher protein productivity per integrated copy (economic for cell);
4. Versatile: can be used in any strain;
5. Integration platforms can be created for all sorts of desired genes without the need to address adverse effects of integration over and over;
6. Integration platforms can be created in highly expressed domains of the genome;
7. Useful domains can be re-used facilitating in regulatory approval for production strains.

The following patent applications may serve to indicate the general level of skill in the art and merely serve to illustrate the fields of application of the current invention.
EP 0 068 740 (Jan. 5, 1983) "RECOMBINANT DNA CLONING VECTORS AND THE EUKARYOTIC AND PROKARYOTIC TRANSFORMANTS THEREOF", illustrating the use of yeast selectable markers, such as hygromycin-B, G418- resistance and the like;
EP 0 077 689 (Apr. 27, 1983) "METHOD OF GENE MANIPULATION USING AN EUKARYOTIC CELL AS THE HOST", illustrating the use of a 3'-leader for expression of DNA in higher eukaryotic cell, such as yeasts and fungi;
EP 0 088 632 (Sep. 14, 1983) "EXPRESSION, PROCESSING AND SECRETION OF HETEROLOGOUS PROTEIN BY YEAST", illustrating the use of homologous signal peptides for secretion in Saccharomyces species;
EP 0 096 910 (Dec. 28, 1983) "YEAST OF THE GENUS KLUYVEROMYCES MODIFIED FOR THE EXPRESSION OF PREPROTHAUMATIN OR ITS VARIOUS ALLELIC AND MODIFIED FORMS OR THEIR MATURATION FORMS" illustrating the cloning and expression of foreign genes in the yeast Kluyveromyces;
EP 0 123 811 (Jun. 12, 1991) "THE USE OF THE GAL 1 YEAST PROMOTER";
EP 0 127 304 (Dec. 5, 1984) "PROCESS FOR PRODUCING HETEROLOGOUS PROTEIN IN YEAST, EXPRESSION VEHICLE THEREFOR, AND YEAST TRANSFORMED THEREWITH", illustrating secretion in Saccharomyces using the invertase signal peptide;
EP 0 123 544 (Oct. 31, 1984) "PROCESS FOR EXPRESSING HETEROLOGOUS PROTEIN IN YEAST, EXPRESSION VEHICLES AND YEAST ORGANISMS THEREFOR", illustrating the use of the alfa-factor leader/signal peptide in Saccharomyces cerevisae;
"EP 0 139 383 (May 2, 1985) "METHOD FOR EXPRESSING FOREIGN GENES IN SCHIZOSACCHAROMYCES POMBE AND THE USE IN THERAPEUTIC FORMULATIONS OF THE PRODUCTS, DNA CONSTRUCTS AND TRANSFORMANT STRAINS OF SCHIZOSACCHAROMYCES POMBE USABLE IN SUCH METHOD AND THEIR PREPARATION";
U.S. Pat. No. 4,745,062 (PLASMID VECTORS FOR CLONING AND EXPRESSION OF A PROTEIN IN A MICROORGANISM, COMPRISING AT LEAST ONE PROMOTER FOR EXPRESSION OF B-GLUCOSIDASE IN YEASTS; MICROORGANISMS CONTAINING THESE PLASMIDS; A FERMENTATION PROCESS AND THE ENZYMES OBTAINED", illustrating over-expression of a β-D-glucosidase in Saccharomyces cerevisiae;
EP 0 164 556 (Dec. 18, 1985) "ENHANCED YEAST TRANSCRIPTION EMPLOYING HYBRID PROMOTER REGION CONSTRUCTS", illustrating the use of hybrid promoters in yeast gene expression;
EP 0 707 068 (Apr. 17, 1996) "Yeast vector", illustrating a yeast selection marker, the G418 resistance marker of Tn903;
EP 0 163 491 (Dec. 4, 1985) "YEAST VECTOR", illustrating the transformation of non-haploid industrial strains of the yeasts Saccharomyces cerevisiae and carlsbergensis;
EP 0 183 070 (Oct. 9, 1991) "TRANSFORMATION OF YEASTS OF THE GENUS PICHIA", illustrating cloning and expression of genes in the yeast Pichia, using histidine auxotrophic mutants;
EP 0 213 593 (Apr. 10, 1991) "REPRESSIBLE YEAST PROMOTERS", illustrating the use of some repressible yeast promoters in heterologous protein production, such as the hybrid acid phosphatase (PHO5): GAPDH promoter;
EP 0 301 669 (Feb. 1, 1989) "DNA CONSTRUCTS CONTAINING A KLUYVEROMYCES ALPHA-FACTOR LEADER SEQUENCE FOR DIRECTING SECRETION OF HETEROLOGOUS DERIVATIVES" and EP 0 301 670 (Feb. 1, 1989) "KLUYVEROMYCES AS A HOST STRAIN", illustrating secretion of foreign proteins in Kluyveromyces using the various leaders and signal peptides, such as the alpha-factor leader from Kluyveromyces;
WO 90 05787 (May 31, 1990) "POSITION-SPECIFIC INSERTION VECTORS AND METHOD OF USING SAME", illustrating yeast integration vectors based on Ty3 in Saccharomyces cerevisiae;
EP 0 394 538 (Oct. 31, 1990) "A YEAST CELL OF THE GENUS SCHWANNIOMYCES", illustrating cloning and expression of foreign genes in the yeast Schwanniomyces;
WO 90/14423 (Nov. 29, 1990) "MICROORGANISM TRANSFORMATION", illustrating yeast transformation by the use of integration by linear vector having regions of homology at the extremities of the linearised vector;
NL 9001159 (Dec. 16, 1991) "Methode om de efficientie van de secretie van eiwitten door gistcellen te vergroten", illustrates Kluyveromyces and Saccharomyces mutants with improved secretion due to permeable cell walls;
EP 0 531 187 (Mar. 10, 1993) "PROMOTEUR DE LEVURE ET SON UTILISATION", discloses the yeast ADH4 (alcohol dehydrogenase) promoter for foreign gene expression in yeast, such as Kluyveromyces lactis;
WO 94 01570 (Jan. 20, 1994) "K. lactis rp28 RIBOSOMAL PROTEIN GENE PROMOTER AND USE THEREOF", WO 94 01569 (Jan. 20, 1994) "K. lactis PYRUVATE DECARBOXYLASE PROMOTER GENE AND USE THEREOF", WO 94 03618" (Feb. 17, 1994) "K. lactis TRANSALDOLASE GENE PROMOTER AND USE THEREOF" and WO 94 13821 (Jun. 23, 1994) "THE USE OF THE KLUYVEROMYCES MARXIANUS INULINASE GENE PROMOTER FOR PROTEIN PRODUCTION", illustrate the use of other promoters for foreign gene expression in the yeast Kluyveromyces lactis;
ES 2 059 280 (Nov. 1, 1994) "WINE YEAST CECT1973 RECOMBINANT FOR T. LONGIBRACHIATUM ENDOGLUCANASE", illustrates wine yeast strain improvement by cloning and expression of the endoglucanase from Trichoderma longibrachiatum in Saccharomyces cerevisiae under the control of the actin promoter;
EP 0 751 997 (Sep. 28, 1995) "DNA ENCODING ENZYMES OF THE GLYCOLYTIC PATHWAY FOR USE IN ALCOHOL PRODUCING YEAST", illustrating yeast strain improvement by genetic engineering of the Entner-Doudoroff pathway;

EP 0 748 872 (Dec. 18, 1996) "STRAINS OF BAKERY YEAST CAPABLE OF EXPRESSING AND EXPORTING TO THE CELLULAR EXTERIOR THE ENZYME A-(1-4)-AMYLASE OF ASPERGILLUS ORYZAE: PRODUCTION PROCESS AND APPLICATION", illustrating improvement of Saccharomyces cerevisiae for bakery purposes using recDNA techniques, such as cloning and expression of alpha-amylase from Aspergillus oryzae in baker's yeast;

EP 0 096 430 (May 19, 1983) "CLONING SYSTEM FOR KLUYVEROMYCES SPECIES", illustrates the transformation of the genus Kluyveromyces.

EP 0 301 670 (Jul. 28, 1988) "KLUYVEROMYCES AS A HOST STRAIN", illustrates the use of the genus Kluyveromyces for the secretion of proteins.

The following examples serve to further illustrate the invention.

EXAMPLES

Experimental
Oligo's
AB 5677: 5'CATTGCTGTTTTACTTGAGATTTC 3' [SEQ. ID NO. 1]
AB 5678: 5'AATTGGTTTACCGTACTTCCAGTC 3 [SEQ. ID No. 2]
oligo LACP1 (also designated P1): 5'ATCTATCTGT TCCTTTCCTT 3' [SEQ. ID NO. 3]
oligo LACT1 (also designated T1): GTATGTACTT ACAG-GTATAT [SEQ. ID. NO. 4]
amdS oligo's
Oligo's AB3514 and AB3515 (see patent application EP 0 635 574 A1)
no. 4596: 5'TTCTCTTATAGTCGACTCTAATTCT-TCTAAGCTTCTACCC 3'
no. 4597: 5'TTCCTTTGGTTACTAGTATCGTC 3' [SEQ. ID NO. 6]
no. 4719: 5'CCAATGCAATCCATGTACTCAAC 3' [SEQ. ID NO. 7]
no. 4720: 5'TAATTCTGCATCGATCCAGTATG 3' [SEQ. ID NO. 8]

Lactase Assay
β-Galactosidase (lactase) activity was determined according to Miller (Experiments in molecular genetics—Cold Spring Harbor Laboratory Press (1972) pp 352–355) using Z buffer and o-nitrophenyl-β-D-galactopyranoside as substrate. Cells were harvested by centrifugation and resuspended in Z buffer. They were disrupted by vortexing during 3×1 minutes with glass beads and intermediate cooling. Glass beads and cell debris were removed by 5 min centrifugation at 13 000×g and the supernatant, recentrifuged 15 min at 13 000×g, was used for the assays.

Chymosin Assay
Culture medium was acidified to pH 2 by the addition of 1 M $H_2SO_4$ and incubated for 2 hrs at room temperature. Neutralization to pH 6 was performed by the addition of 2 M Tris base. A 50 µl volume of an appropriate dilution was added to 200 µl of a suspension of 12% non-fat dry milk in 10 mM $CaCl_2$ and incubated at 37° C. until a clot formed. A unit of chymosin activity is defined as the amount of active chymosin required to produce a clot in 10 min under these conditions.

Selection on Acetamide Minimal Medium
1. amdS⁺ strains were growth in YEPD (10 g/l yeast extract; 20 g/l bacto pepton; 2% glucose) for 48 hours at 30° C. and 300 rpm.
2. Cell culture was diluted in 0.9% NaCl. 50–100 cells were plated on a YEPD agar plate.
3. Plates were incubated for 2 days (if necessary 3 days at 30° C. and then replica-plated to acetamide agar-plates (below)
5. Plates were incubated 48 hours at 30° C.
6. amdS⁻ colonies were re-streaked on YEPD agar plates.

Transverse Alternating Field Eletrophoresis (TAFE)
Agarose plugs of K. lactis were prepared as described by Schwartz and Cantor (Cell 37, (1984) p. 67 et seq.). The TAFE was performed with a Beckman Geneline II according to the System Operating Instructions. Conditions: 1% agarose, 1×TAFE-buffer, 22 hours, 250 V, Switch A 4 sec, Switch B 4 sec.

PCR Protocol
A standard PCR protocol consists of 25 cycli of 1 min 94° C.; 1 min 55° C. and 1,5 min 72° C.

PCR on K. lactis Cells
with a Gilson P20 automatic pipette, part of a yeast colony was resuspended in 30 µl $H_2O$
To prevent evaporation a drop of mineral oil was added
The cell suspension was incubated 15 minutes at 98° C.
The temperature was reduced to 72° C.
20 µl of the following reaction mixture was added:
dNTP mix: final concentration in PCR reaction: 200 µm of each nucleotide dATP, dCTP, dGTP, dTTP
dVB: final concentration in PCR reaction:
1 mM Tris-HCl pH8,0
1 mM NaCl
0,1 mM EDTA Super TAQ
Reaction buffer: final concentration in PCR reaction:
10 mM Tris-HCL pH9,0
1,5 mM $MgCl_2$
50 mm KCl
0,01% (W/V) gelatin
Super TAQ DNA polymerase 0,2 units per reaction
PCR was started using the following program:
45" at 94° C.
45" at 55° C.
2' at 72° C.
25 cycles followed by 1 step: 7' at 72° C.

Strains and Media
E. coli strain GM 48 (dam⁻): ATCC 39099
Media For lactase and chymosin determinations CBS 685.97 was grown up in a medium containing 10 g/l yeast extract; 20 g/l bacto pepton and 2% galactose.
YCB acetamide plates contained 1.2% oxoid agar, 1×YCB (Yeast carbon base from Difco), 30 mM K-$PO_4$ buffer pH 6.8, 5 mM acetamide (Sigma). Standard Molecular Biological procedures were carried out according to Sambrook et al. in Molecular Cloning: a Laboratory Manual, 2nd Edition (1989; Cold Spring Harbor Laboratory Press).

Example 1

Construction pGB LACamdS1
a. Plasmid pUCla56
Chromosomal DNA was isolated from K. lactis strain CBS 685.97 by standard procedures (Struhl et al. Poc. Natl. Acad. Sci.USA 76 (1979) 1035–1039). The DNA was cleaved with XbaI and cloned in plasmid pUC18 cleaved with XbaI and phosphatase treated. A lactase gene containing clone was picked up as described by Dickson and Markin (Cell 15 (1978, 123–130). The resulting clone contained two copies of pUC 18 in tandem (FIG. 1.)

b. Plasmid pGB G418 LAC

Figure 2:
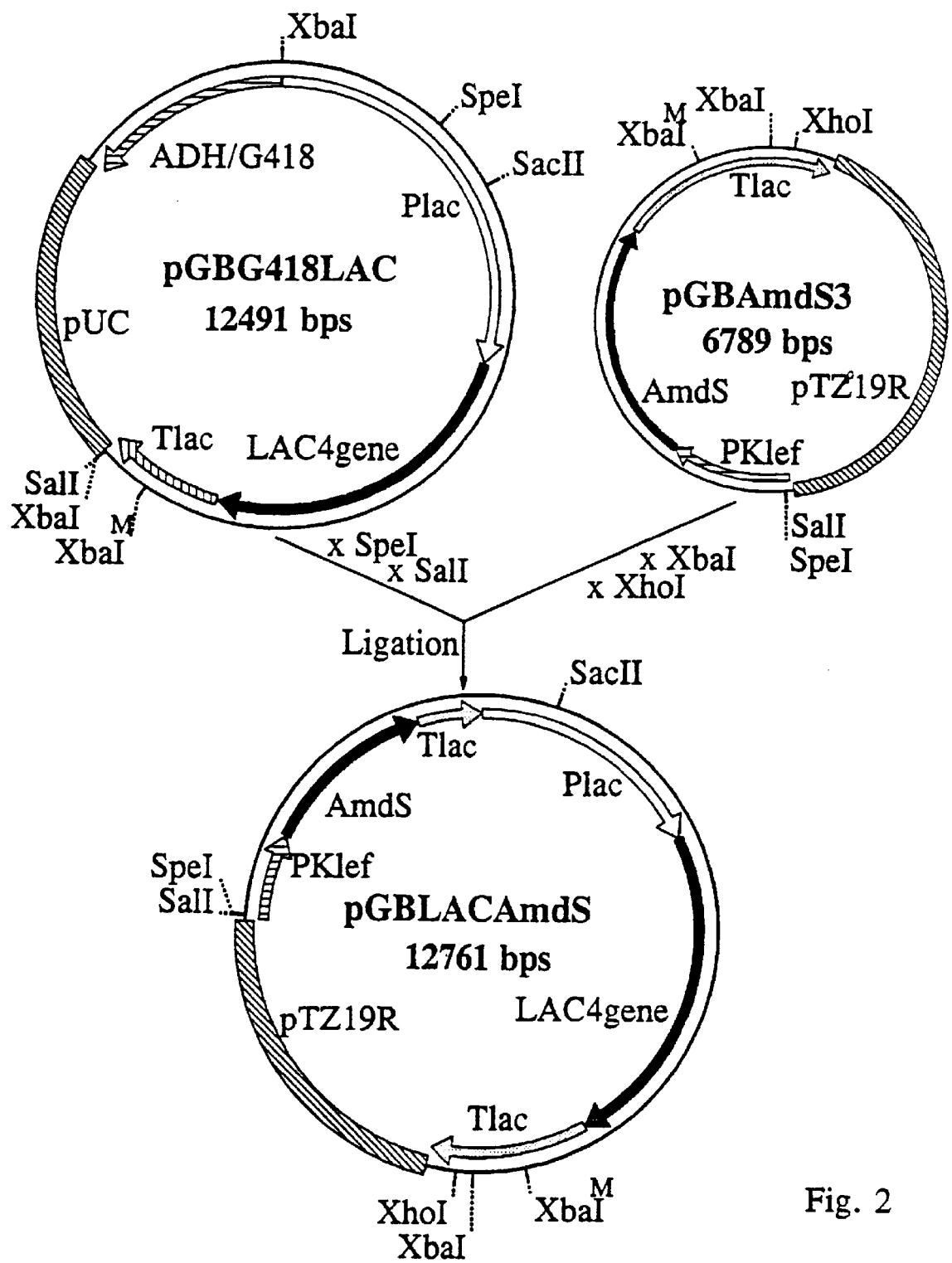
FIG. 2: Construction pathway of pGBLACAmdS (XbaI M=methylated in *E. coli* JM109)

Plasmid pUCla56 was cleaved with XbaI and the fragment containing the LAC4 gene was cloned in the unique XbaI site of plasmid pUCG481-1 (Van den Berg et al., EP 0301 670) yielding plasmid pGB G418 LAC. (FIG. 1.).

c. Construction of pGBLAmdS pGBLACAmdS was constructed by cloning the SpeI/SalI $P_{lac4}$/-LAC4/$T_{lac4}$ fragment of pGBG418LAC into XbaI/XhoI sites of pGBamdS-3 vector (Selten et al., EP 0 635 574). By this construction the amdS marker and the E.coli sequences were cloned between LAC4 terminator repeats. Before pGBamdS-3 could be digested with XbaI the vector was transformed to E.coli GM48 to remove the methylation of the XbaI site. For easier isolation of the SpeI/SalI $P_{lac4}$/LAC4/$T_{lac4}$ fragment of pGBG418LAC this vector was also digested with SacI which digested pUCG418 in 2 parts. 16 E.coli JM109 colonies were obtained. Plasmid DNA was isolated and checked by restriction analyses and all clones had the correct structure. One of these clones is called pGBLACAmdS (FIG. 2).

Example II

Construction of the 3 Copy Lactase Strain LCT 105 a. Transformation of pGBLACAmdS to CBS 685.97 pGBLACAmdS was digested with SacII and transformed to CBS 685.97 by the method of Ito et al. (J. Bact 153 (1983) 163–168). The vector still contains E. coli sequences which will be integrated into the yeast genome but can be removed together with the amdS marker afterwards (Selten et al. (op.cit)). Transformants were selected on YCB/acetamide plates. After 3 days of growth at 30° C. many transformants were visible.

b. Genomic analysis of the pGBLACAmdS transformants

Figure 3:
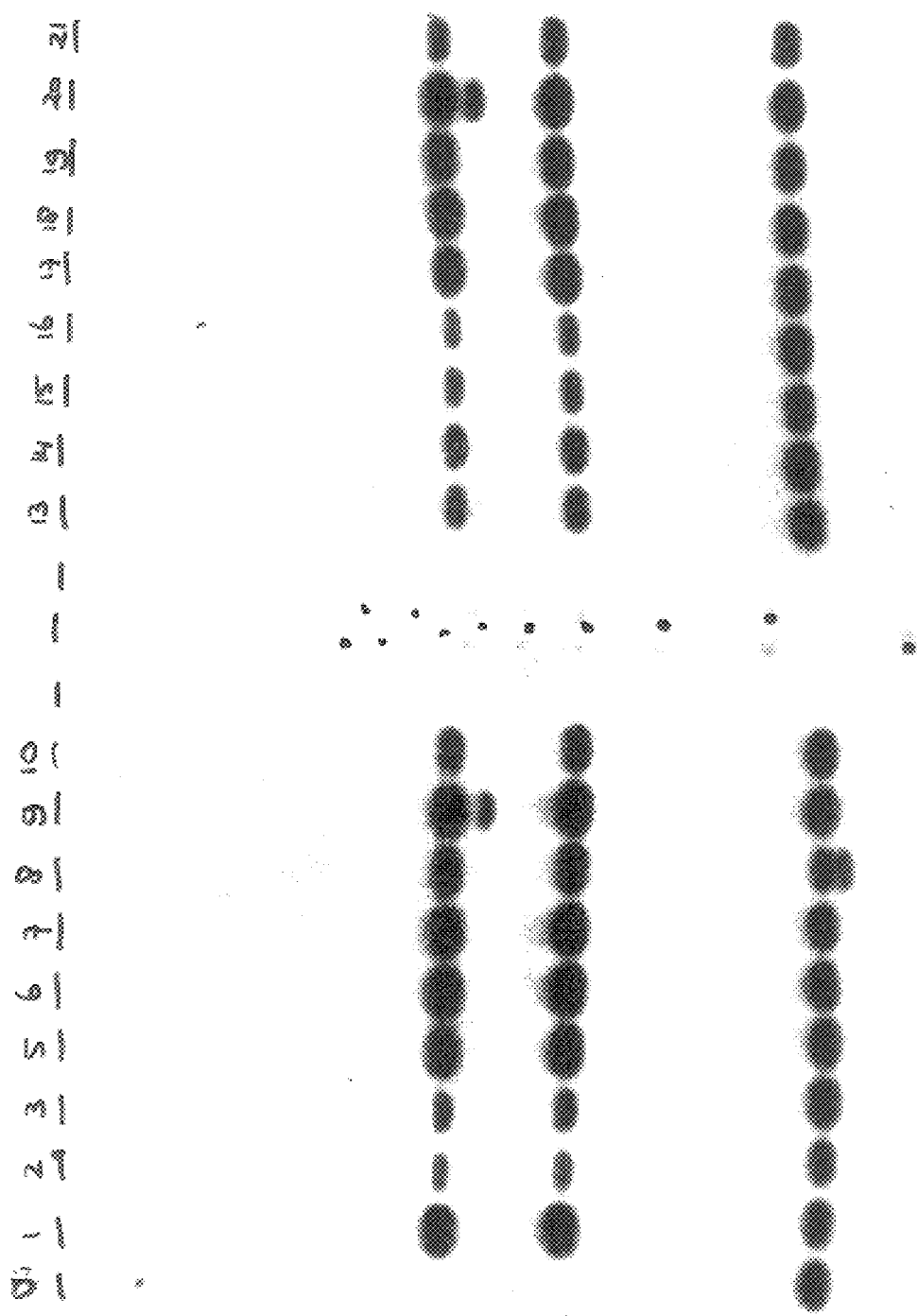
FIG. 3 The result of the exposed X-ray film of KpnI digested genomic DNA of CBS 685.97 and 18 pGBLACAmdS-1 transformants of CBS 685.97 after hybridization with LacT-probe; For LacT probe see FIG. 4. Lane 0 is control lane. Lanes 1–10 and lanes 13 to 21 are independent transformants.
Figure 4A:
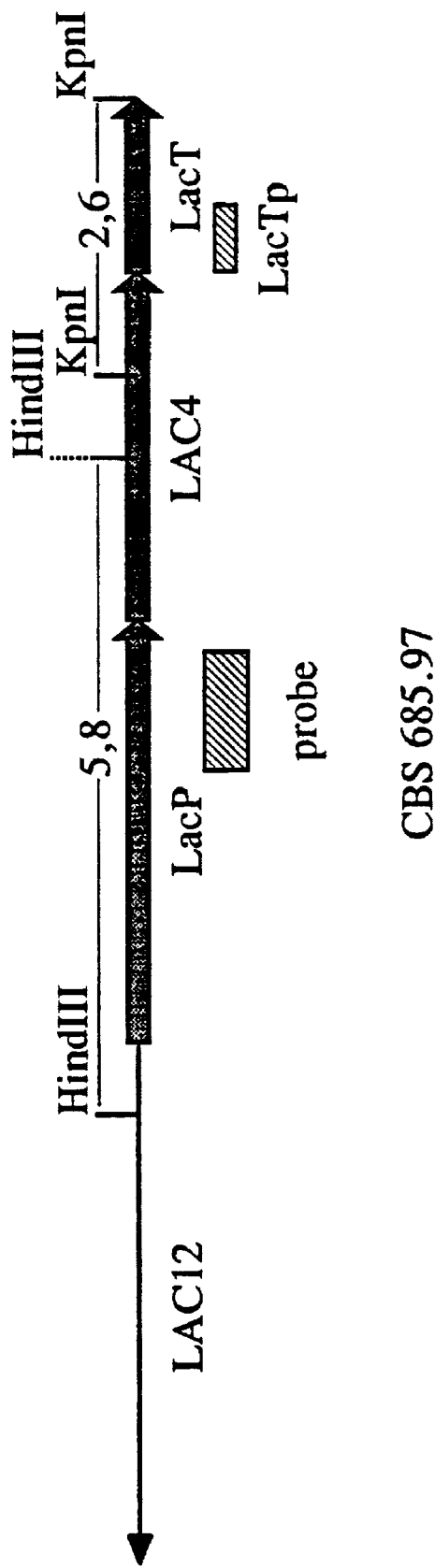
FIG. 4a: Schematic representation of the chromosomal structure of the LAC4 locus in strain CBS 685.97

Southern analysis was performed on 18 pGBLACAmdS transformants and on CBS 685.97 (see FIGS. 3 and 4). 15 Transformants showed the expected fragments for correct integration of pGBLACAmdS and 3 transformants showed in addition to the expected fragments for correct integration, another fragment which means that the pGBLACAmdS construct is (also) integrated elsewhere into the genome (16% random integration in case of transformants AmdS-8, -9 and -20). Also some estimations were made about the pGBLACAmdS copynumber of the transformants (Table I). It was surprisingly found that strain CBS 685.97 contains 2 endogenous LAC4 genes. So, the total number of LAC4 gene copies is easily found by adding up the pGBKLACAmdS copynumber and these 2 endogenous LAC4 genes (Table I). The number of transformants which have a given LAC4 copynumber was calculated as a percentage of the total number of transformants tested (18) and is also given in Table 1.

TABLE 1 pGBLACAmdS transformants with the estimated pGBLACAmdS copynumber, the total number of LAC4 genes and the percentage of that number of transformants which have the same pGBLACAmdS copynumber.

| Transformant # | pGBLACAmdS copynumber | Total number of LAC4 genes | Percentage |
|---|---|---|---|
| 2, 3, 13, 14, 15, 16 | 1 | 3 | 33% |
| 5, 10, 21 | 2 | 4 | 33% |
| 6, 7, 19 | 2–3 | 4–5 | |
| 1, 17, 18 | 3–4 | 5–7 | 16% |

Figure 5:
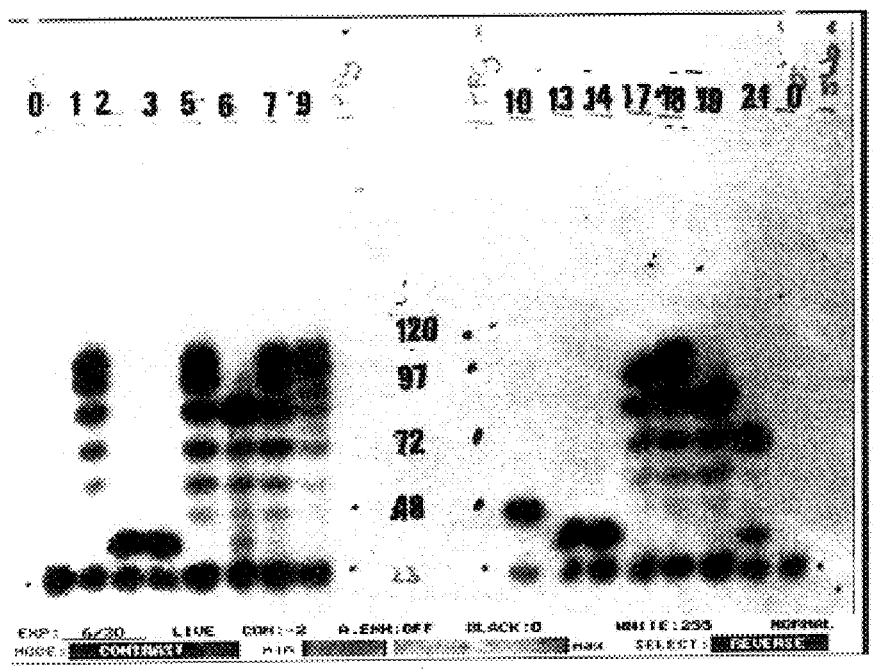
FIG. 5: The result of MluI digested genomic DNA of CBS 685.97 and 14 pGBLACAmdS transformants of CBS 685.97 after hybridization with LacP-probe; For LacP probe see FIG. 4. Lane 0 is control lane. Lanes 1–9 and lanes 10–21 are independent transformants. Numbers between lanes 9 and 10 represent the size of marker fragments in kilo base pairs.

With TAFE the LAC4 copynumber of 14 pGBLACAmdS transformants was determined more precisely (FIG. 5). The pGBLACAmdS copynumber and the total number of LAC4 genes present in the transformants is presented in Table 2. The transformants AmdS-1, -5, -6, -7, -9, -17, -18, -19 and -21 showed in addition a fragment of 23 kb many other fragments representing many integrated pGBLACAmdS copies in one of the two endogenous LAC4 loci. However these copies are not stable as shown by the hybridization pattern in FIG. 5.

TABLE 2 pGBLACAmdS copynumber of some pGBLACAmdS transformants determined by TAFE and the total number of LAC4 genes.

| Transformants # | pGBLACAmdS copynumber | Total number of LAC4 genes |
|---|---|---|
| 2, 3, 13, 14 | 1 | 3 |
| 10 | 2 | 4 |
| 21 | 4 (not stable) | 6 (not stable) |
| 6, 19 | 5 (not stable) | 7 (not stable) |
| 17 | 6 (not stable) | 8 (not stable) |
| 1, 5, 7, 9, 18 | 7 (not stable) | 9 (not stable) |

Transformants 2 and 13 were stored as LCT 101 and LCT 102, respectively c. Isolation of a 3 copy marker-free strain A heterologous-DNA-free strain with 3 lactase gene copies can be obtained via an internal out-recombination on the LAC4 terminator repeats. A correct internal out-recombination on the LAC4 terminator repeats (FIG. 4) results in the deletion of all the heterologous DNA sequences (pTZ19R and KIef/amdS). This results in a heterologous DNA-free strain with 1 extra lactase gene copy. The loss of the acetamidase gene was used for the selection of heterologous DNA free strains.

Figure 4B:
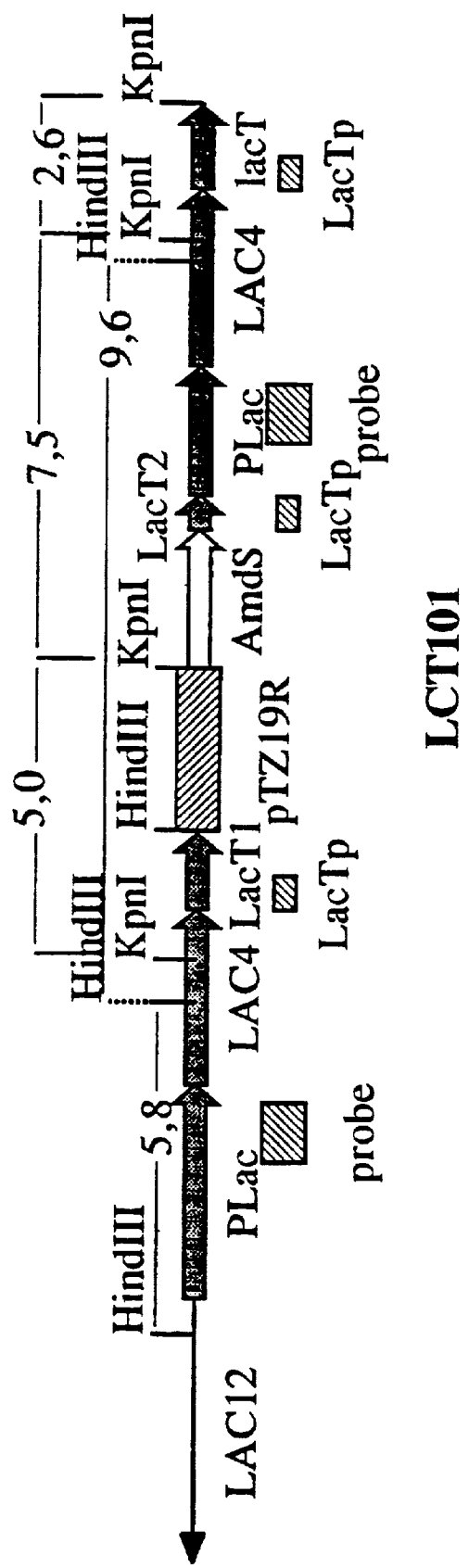
FIG. 4b: Schematic representation of the chromosomal structure of the LAC4 locus in strain LCT101, which is strain CBS 685.97 transformed with pBGLACAmdS-1.
Figure 4C:
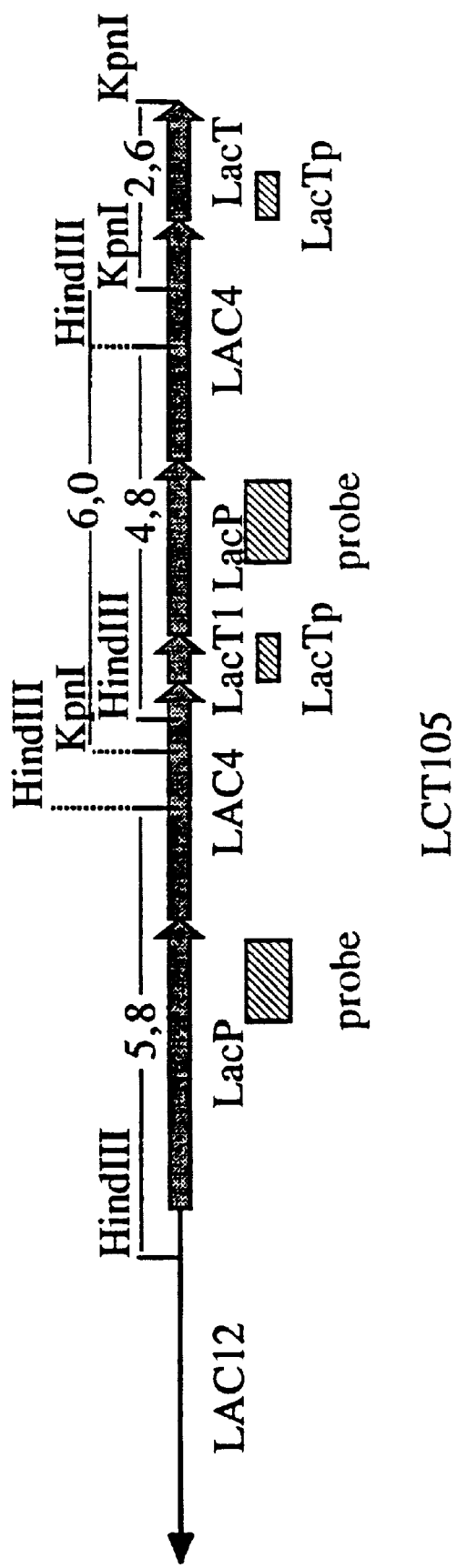
FIG. 4c: Schematic representation of the chromosomal structure of the LAC4 locus in strain LCT105, which is LCT101 after out-recombination of heterologous DNA over LacT1 and LacT2. Symbols: LacP: LAC4 promoter; LAC4: lactase coding sequences; lacT1, lacT2, lacT: LAC4 terminator sequences; probe: LAC4 promoter probe; LacTp: LAC4 terminator probe. Numbers above figures indicate the length of the relevant restriction fragments used to determine the structure of the DNA locus. Only relevant restriction sites are indicated.

AmdS derivatives have been isolated via negative selection on acetamide plates. Around 1% of the total cell number had lost the acetamidase gene To select an out-recombinant which has maintained 3 lactase gene copies the amdS⁻derivatives were screened by PCR, with oligo LACT1 and oligo LACP1, The position of these oligo's is indicated in FIG. 4c. Only amdS⁻strains with at least 1 extra lactase gene copy tandemly integrated at one of the LAC4 loci can give a PCR fragment of around 600 bp. Around 100 derivatives have been screened by PCR from which 25 derivatives were amdS⁻. Only 1 out of these 25 amdS⁻ derivatives gave a PCR fragment of 600 bp. From this strain the lactase production in shake flask was determined. The lactase production was comparable to the production of LCT101. The new strain was designated LCT105.

LCT105 was further analysed by Southern-blotting. Chromosomal DNA was digested with KpnI and hybridized to the LAC4 promoter probe: the expected hybridization pattern was found. FIGS. 4b and 4c is a schematic representation of the chromosomal structure in LCT101 and LCT105, the LAC4 promoter probe and the length of the hybridizing fragments are indicated.

From these results we conclude that the new strain was free from heterologous DNA. It contains one extra lactase gene copy at one of the two LAC4 loci.

Example III
Isolation of the 4 Copy Lactase Strains LCT 108 and LCT 109 a. Strategy

For the isolation of a 4 copy marker free lactase production strain, LCT105 was transformed with PGBLACamdS. 2 Transformants with different chromosomal structures have been isolated:

In strain LCT106 pGBLACamdS is integrated at the LAC4 locus containing only the endogenous LAC4 gene. So this strain has 2 lactase gene copies in each LAC locus.

LCT107 has the pGBLACamdS copy tandemly integrated at the LAC4 locus which already contains 2 lactase gene copies.

LCT108 is a 4 copy amdS⁻derivative from LCT106 and LCT109 is a 4 copy amdS⁻derivative from LCT107.

b. Transformation of LCT105

LCT105 was transformed with pGBLACamdS using the procedure of Ito et al (op cit.) Transformants were plated out on acetamide plates and subsequently on YEPD agar plates.

From 40 transformants the lactase production in shake flask was determined. 15 to 20% of the transformants had a lactase production as expected for a 4 copy strain. The rest of the transformants had a lower lactase production.

Transformants with a lactase production equally or higher than LCT-105, have been analysed by Southern-blotting. Chromosomal DNA's were digested with KpnI; hybridizations were performed with the LAC4 promoter probe indicated in the physical map of FIG. 4c. All transformants showed the hybridization pattern as expected. The intensity of the 7.5 kb band is a measure for the number of PGBLA-CamdS copies integrated.

To determine the exact copy number and chromosomal structure 15 transformants have been further analysed by TAFE.

Chromosomal DNA was digested with MluI which does not cut in pGBLACamdS. So the length of the hybridising fragments is a measure for the copy-number. Two transformants have been stored;

LCT106 has 2 lactase gene copies in each LAC4 locus.
LCT107 has 3 copies in one LAC4 locus and 1 copy in the other locus.

c. Isolation of two marker-free 4 copy strains

Both 4 copy strains LCT106 and LCT107 were screened for amdS⁻derivatives on acetamide minimal plates as described above. From strain LCT106 10000 colonies were screened. Around 150 amdS⁻colonies were found. From strain LCT107 around 15000 colonies were screened. Around 300 amdS⁻colonies have been isolated.

For the isolation of a 4 copy marker free strain all the amdS⁻isolates have been tested for their lactase production. Isolates with a lactase production comparable to that of the host-strains, 15 from LCT106 and 2 from LCT107 have been further analysed. From these strains the lactase production in shake flask was determined once more. Most of the isolates had a lactase production comparable to the production of LCT106 or LCT107. Chromosomal DNA was analysed with KpnI; all isolates showed the expected hybridization pattern. From results of Southern blots of normal (KpnI digest) and TAFE (MluI digest) gels we conclude that all the amdS⁻isolates were heterologous DNA free and that they had the correct chromosomal structure. Isolate 123, a derivative from strain LCT106 was designated LCT108 and isolate 549, a LCT107 derivative, was designated LCT109.

Example IV
Isolation of the 6 Lactase Copy Strains LCT124 and LCT126 a. Strategy

For the isolation of a 6 copy marker-free strain LCT109 was transformed with pGBLACamdS. A 1 copy transformant with the pGBLACamdS expression-vector tandemly integrated at the LAC4 locus with only one LAC4 gene copy was selected. A transformant with such a chromosomal structure has the advantage that in 1 selection round a 6-copy marker-free strain can be isolated from a 4 copy strain via gene conversion.

b. Transformation of LCT109

Strain LCT109 was transformed with pGBLACamdS according to the method of Ito (op cit.). 46 transformants were first restreaked on acetamide minimal plates and subsequently on YEPD plates.

To select transformants with only one pGBLACamdS copy, the lactase production of these transformants was determined in shake flask. All 46 transformants had a lactase production equal or above the lactase production of the host strain LCT 109. To select a strain with a suitable chromosomal structure, i.e. the pGBLA-CamdS copy tandemly integrated at the LAC4 locus with only 1 LAC4 gene copy, chromosomal DNA was analysed with MluI. This enzyme does not cut in the lactase expression cassette. So the length of the hybridizing fragment is a measure for the number of copies which are tandemly integrated. Digested DNA was separated by TAFE, Southern blotted and finally hybridized with the LAC4 promoter probe. Two transformants with the correct chromosomal structure were stored as LCT-111a and LCT111b.

Isolation of a 6-copy marker-free strain via gene conversion

Around 20000 colonies from strain LCT111a have been screened for amdS⁻derivatives by selection on acetamide plus and minus plates.

Around 200 amdS⁻derivatives were isolated from the LCT111a strain

To isolate marker-free strains with at least 5 lactase copies we have determined the lactase production for the amdS⁻isolates in shake flasks.

10 isolates from LCT111a had a lactase production comparable to or higher than LCT111a. They were further analysed by Southern-blotting and TAFE (MluI digest) to determine their copy numbers and chromosomal structure. The exact copy number of 7 strains was determined by TAFE. Six out of seven strains (LCT 120 through 125) had 6 lactase gene copies with in each locus 3 copies tandemly integrated. Strain LCT126 had also 6 copies but in one LAC4 locus 2 copies and in the other one 4 copies tandemly integrated. The results: copy number and lactase production of the different strains are summarized in table 2. No 5 copy marker free strain could be isolated; in none of the isolates a correct out-recombination had occurred. Strains LCT120 to LCT126 originated from a gene-conversion. The chromosomal structure of LCT125 (2 copies in one and 4 copies in the other locus tandemly integrated) cannot be explained via gene conversion.

Example V
Determination of Lactase Production Levels in Shake Flasks

Lactase production levels of various strains were determined after centrifugation of the cells. The results of these determinations are presented in Table 3. It is clear that there is a correlation between LAC4-gene copy number and lactase expression level up to 5 copies. At higher copy numbers the LAC4-gene expression levels off.

TABLE 3

Review of the copy number, copy number distribution (indicated between brackets) and the lactase production in shake flask from the multi-copy lactase production strains. Copy numbers determined by TAFE are more reliable than by Southern analysis.

| Name | copynumber (Southern) | copynumber (TAFE) | amdS | relative lactase prod. |
|---|---|---|---|---|
| CBS 685.97 | 2 | | | 100 |
| LCT101 | 3 | 3(1 + 2) | + | 147 |
| LCT105 | 3 | 4(1 + 3) | − | 144 |
| LCT106 | 4 | 4(2 + 2) | + | 193 |
| LCT107 | 4 | 4(1 + 3) | + | 188 |
| LCT108 | 4 | 4(2 + 2) | − | 175 |
| LCT109 | 4 | 4(1 + 3) | − | 185 |
| LCT111a | 5 | 5(2 + 3) | + | 222 |
| LCT111b | 5 | 5(2 + 3) | + | 206 |
| LCT120 | 5 | 6(3 + 3) | − | 229 |
| LCT121 | 6 | 6(3 + 3) | − | 232 |
| LCT122 | 9 | 6(3 + 3) | − | 231 |
| LCT123 | 6 | 6(3 + 3) | − | 236 |
| LCT124 | 6 | 6(3 + 3) | − | 244 |
| LCT125 | 6 | 6(3 + 3) | − | 235 |
| LCT126 | 6 | 6(2 + 4) | − | 245 |

Example VI
Confirmation of Chromosomal Structure of 3,4 and 6 Copy Strains LCT105, LCT108, LCT109, LCT121 and LCT124

To confirm that strains LCT105, LCT108, LCT109, LCT121, LCT124 and LCT125 are free from foreign DNA hybridization with different probes have been performed. All the probes, Klef promoter, complete amdS cDNA and pTZ19R showed the expected pattern.

Example VII
Plasmid pGBAmdS 61

Figure 6:
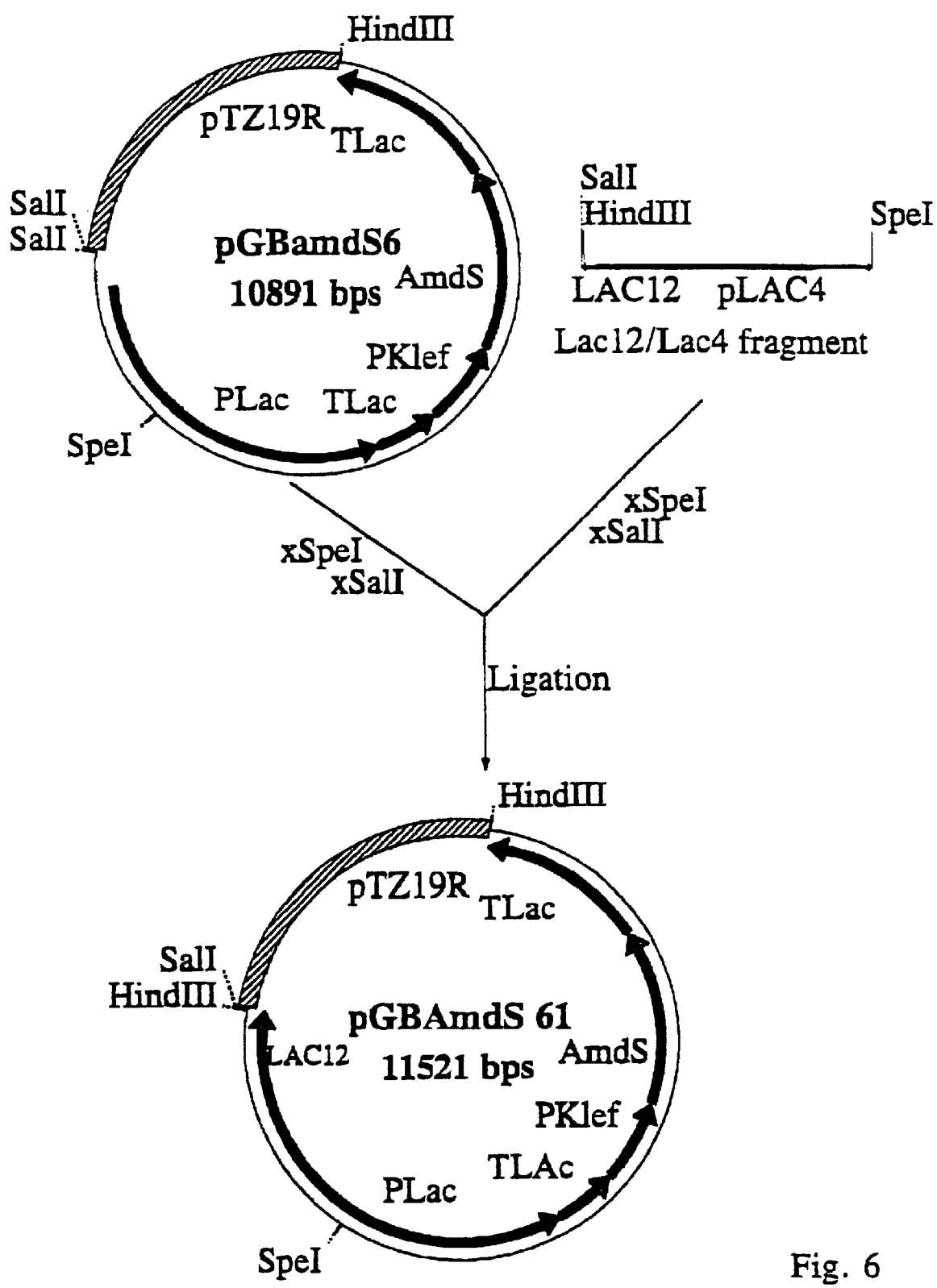
FIG. 6: Construction pathway for pGBamdS 61.

Plasmid pGBamdS 6 (Selten et al. op.cit) was cleaved with SalI and SpeI and the 9kb fragment was isolated by a Qiagen gel extraction kit. Oligo's 4596 and 4597 were PCR primed on chromosomal DNA from strain CBS 685.97 isolated by the method of Das & Hollenberg (1982, Current Genet. 5, 123–128). The 2 kb fragment which resulted was isolated by a Qiagen gel extraction kit. After digestion with SalI and SpeI the fragment was ligated to the 9kb fragment described above, resulting in plasmid pGBamdS 61 (FIG. 6).

Example VIII
Gene Replacement in Strain CBS 685.97

Plasmid pGBAmdS 61 was cleaved with Hind III and extracted with phenol, followed by ethanol precipitation before transformation. The DNA was dissolved and transformed to CBS 685.97 by the method of Ito et al. (op cit.). Transformants were analysed by PCR on intact K. lactis cells with oligos 4719 and 4720. With these oligo's it is possible to discriminate between gene replacement removing one of the LAC4 genes and an event leading to integration of the plasmid after circularization. The latter event gives rise to an amplified fragment of 700 bp. The strains that did not give rise to such a fragment were grown up on an YCB acetamide agar plates. Chromosomal DNA's were isolated from the transformants, digested with BamHI and hybridized to a LAC4 terminator fragment from EcoRI to Xba|(Breunig et al. Nucleic Acids Res 12 (1984) 2327–2341). The resulting strain was designated K.lactis GBA5.

Example IX
Isolation of K.lactis GBA-CHY01, GBA-CHY02 and GBA-CHY03

K.lactis strain GBA5 was transformed (Ito et al. op cit.) with plasmid pKS-105 (Van den Berg et al. EP 0301670) cleaved with Sst2. Transformants were selected for the presence of G418 and amdS selectable markers. Strains which had integrated 1,2 or 3 copies in the native lactase locus were identified by TAFE after cleavage with MluI. Strains with 1,2 or 3 copies were designated GBA-CHY01, 02 and 03, respectively.

Example X
Isolation of K.lactis GBA-CHY11, GBA-CH22 and GBA-CHY33

Starting strains GBA-CHY01, 02 and 03 were selected for an amdS minus phenotype as described in example IV c. In each case about 5 amdS⁻negative colonies were isolated out of 20.000 colonies plated out on normal YEPD and YEPD acetamide plates (see methods). This resulted in one colony for CHY 01, 02 and 03 each, which had doubled the number of chymosin copies by gene conversion. These colonies were designated GBA-CHY11, 22 and 33 respectively.

Example XI
Isolation of K.lactis GBA-CHY43, GBA-CHY53 and GBA-CHY54

Figure 7:
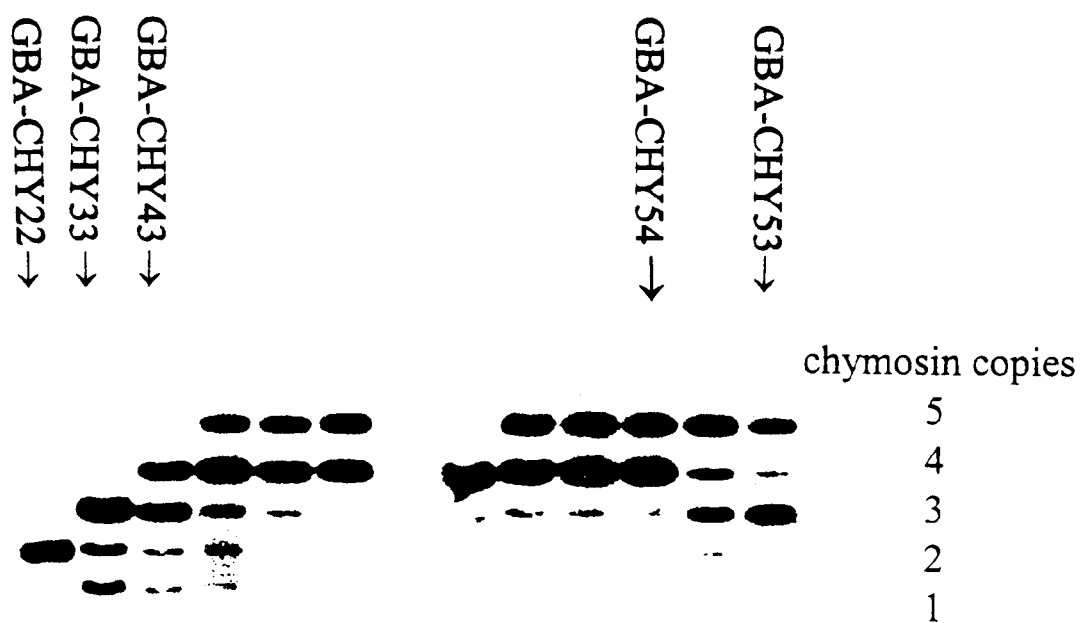
FIG. 7: Results of copynumber analysis of GBA-CHY22, GBA-CHY33, GBA-CHY43, GBA-CHY53 and GBA- CHY54. Chromosomal DNA was digested with MluI and hybridized with the LacP probe. The fragments expected for 1, 2, 3, 4 and 5 copies of the chymosin expression cassette are indicated.
Figure 8:
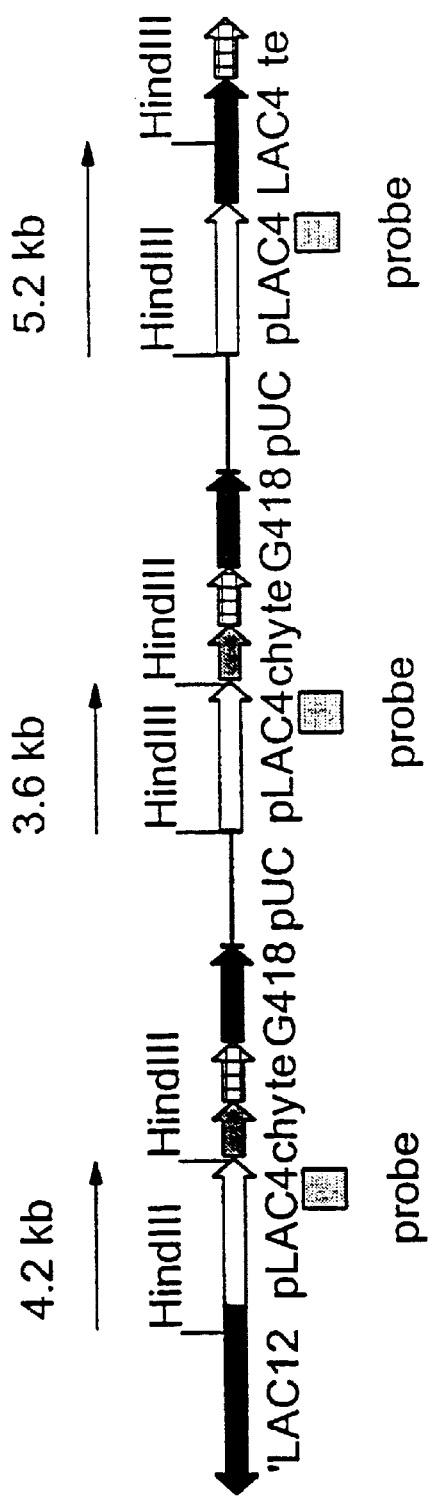
FIG. 8: Schematic presentation of the chromosomal structure of the LAC4 locus with two tandemly integrated chymosin expression cassettes pKS105(strain GBA-CHY22).Symbols: pLAC4: LAC4 promoter; LAC4: lactase coding sequences; te: LAC4 terminator sequence; probe: LAC4 promoter probe. Only relevant restriction sites and the length of the expected fragments are indicated.
Figure 9:
FIG. 9: Result of chromosomal analysis of the GBA-CHY22, GBA-CHY33, GBA-CHY43, GBA-CHY53 and GBA-CHY54 strain. Chromosomal DNA was digested with HindIII and hybridized with the indicated probe. When 3 or more chymosin copies pKS105 are tandemly integrated into the lactase locus the intensity of the 3.6 kb hybridizing fragment is higher.

The 6 integrated copies of the chymosin expression cassette pKS105 (divided equally over the two lactase loci) in the GBA-CHY33 strain were not completely stable (see FIG. 7). In order to isolate a more stable 6 copy strain single colonies of GBA-CHY33 were isolated and analysed for copynumber. The GBA-CHY33 strain was streaked on a YEPD plate for single colony isolation (one purification round). 10 Single colonies of each purification round were analysed at copynumber with the help of Transverse Alternating Field Electrophoresis (TAFE). Agarose plugs containing the chromosomal DNA were digested with the restriction enzym MluI and size-fractionated by TAFE. This enzyme does not cut in the chymosin expression cassette. So the length of the hybridizing fragment is a measure for the number of copies which are tandemly integrated. After transfer to nitrocellulose, hybridization was performed according standard procedures. As probe a LAC4 promoter fragment was used, indicated in the physical map of FIG. 4c. After hybridization we expect only one fragment with the length of 3 chymosin copies (see FIG. 7). In case of instability (loss of chymosin copies) shorter fragments are detected which represent loci with 1 or 0 chymosin copies in the lactase loci. After four purification rounds a more stable 6 copy strain was found. This 6 copy strain was reisolated again and 50 SCI's were analysed for copynumber with TAFE. A 7 copy strain was found among this single colonies, divided as 4 and 3 copies of pKS105 over the two lactase loci (see FIG. 7). This strain was designated GBA-CHY43. Probably one of the chymosin copies was amplified. In the same way a 9 copy strain was found among the 10 single colony isolates of the GBA-CHY43 strain, which was designated GBA-CHY54. The 9 chymosin copies of the GBA-CHY54 strain were divided as 5 and 4 copies of pKS105 over the two lactase loci (see FIG. 7). Among the 9 single colony isolates of the GBA-CHY54 strain an 8 copy strain was found, which was designated GBA-CHY53. The 8 chymosin copies of the GBA-CHY53 strain were divided as 5 and 3 copies of pKS105 over the two lactase loci (see FIG. 7).
Southern analysis was performed to verify whether a deletion in the chymosin expression cassettes of the GBA-CHY22, GBA-CHY33, GBA-CHY43, GBA-CHY53 and GBA-CHY54 strain had occured. Agarose plugs, containing chromosomal DNA was digested with HinDlll and subsequently electrophoresis on a 0.7% agarose gel. After transfer to nitrocellulose hybridization was performed according to standard procedures. As probe a LAC4 promoter fragment was used, indicated in the physical map of FIG. 4c. FIG. 8 is a schematic presentation of the hybridization pattern of GBA-CHY22. The three other strains show the same hybridization pattern, the 3.6 kb hybridizing fragment is characteristic for a tandem repeat of the expression cassette pKS105. In all strains the expected hybridization pattern was found (see FIG. 9). When 3 or more copies of the chymosin expression cassette pKS105 are tandemly integated into the LAC4 locus the intensity of the 3.6 kb hybridizing fragment is higher.

Example XII

Determination of Chymosin Production Levels in Shake Flasks

Chymosin production levels were determined as described in materials and methods after centrifugation of K.lactis cells.

Relative production levels are presented in Table 4.

TABLE 4

Summary of the various chymosin production strains.
In brackets is the copynumber distribution over the two lactase (LAC4) loci as determined by TAFE. The chymosin production level in shake flask of the various chymosin strains is expressed as % of the GBA-CHY11 strain.

| Strain | Copynumber (TAFE) | Relative chymosin production |
|---|---|---|
| GBA-CHY01 | 1 (0 + 1) | 57 |
| GBA-CHY02 | 2 (0 + 2) | 104 |
| GBA-CHY03 | 3 (0 + 3) | 140 |
| GBA-CHY11 | 2 (1 + 1) | 100 |
| GBA-CHY22 | 4 (2 + 2) | 196 |
| GBA-CHY33 | 6 (3 + 3) | 217 |
| GBA-CHY43 | 7 (4 + 3) | 213 |
| GBA-CHY53 | 8 (5 + 3) | 220 |
| GBA-CHY54 | 9 (5 + 4) | 210 |

From the results it is clear that there is a correlation between copynumber of plasmid pKS105 and chymosin production level up to 4 copies. The increase levels off at copynumber above 4.

Deposited Strains

A sample of *Kluyveromyces lactis* having two domains suitable for integration of a desired gene (two LAC4 loci) was deposited on Apr. 11, 1997 under number CBS 685.97 at the Centraal Bureau voor Schimmelcultures, Oosterstraat 1, Baarn, The Netherlands.

What is claimed is:

1. A yeast cell comprising at least two copies of a desired gene integrated into its chromosomes, wherein said chromosome(s) comprise at least two DNA domains each suitable for integration of one or more copies of said desired gene, which domains comprise diploid loci or multiple copies of a single locus and are non-ribosomal RNA encoding DNA domains, and wherein at least two of said non-ribosomal RNA encoding DNA domains have at least one copy of the said desired gene integrated.

2. The yeast cell of claim 1, wherein at least two of said non-ribosomal RNA encoding DNA domains each suitable for integration of one or more copies of said desired gene have two or more copies of the said desired gene integrated.

3. The yeast cell of claim 1 or 2, wherein said non-ribosomal RNA encoding DNA domains have an identical number of copies of the said desired gene integrated.

4. The yeast cell of claim 1, wherein said non-ribosomal RNA encoding DNA domains suitable for integration of one or more copies of said desired gene are duplicates of each other.

5. The yeast cell of claim 1, wherein the yeast cell is a Kluyveromyces yeast cell.

6. The yeast cell of claim 1, wherein the desired gene is a yeast gene.

7. The yeast cell of claim 1, wherein the desired gene is a non-yeast gene.

8. The yeast cell of claim 1, wherein the desired gene is a recombinant gene comprising a transcription promoter region, and optionally further a transcription termination region, functional in the said yeast cell.

9. The yeast cell of claim 1, wherein said desired gene is selected from the group consisting of those coding for lactase, chymosin, phospholipase, insulin, human serum albumin, tissue plasminogen activator, granulocyte colony stimulating factor, interleukins, interferons, a peptide hormone, and a plant cell wall degrading enzyme.

10. The yeast cell of claim 1, wherein the number of non-ribosomal RNA encoding domains suitable for integration of one or more copies of said desired gene is two and the number of copies per domain is at least three.

11. The yeast cell of claim 1, which cell is a selectable marker gene-free yeast cell.

12. A culture of yeast cells, wherein the yeast cells are according to claim 1.

13. A method of producing a protein or peptide, comprising the step of growing a yeast cell according to claim 1 under conditions conducive to the production of said protein or peptide.

14. The yeast cell of claim 4, wherein said nonribosomal RNA encoding DNA domains are allelic form of each other.

15. The yeast cell of claim 5, wherein said non-ribosomal RNA encoding DNA domains are LAC4 alleles.

16. The yeast cell culture of claim 12 stable in its protein, peptide or metabolite productivity for at least about 50 generations without selective pressure.

17. The method of claim 13, further comprising the step of recovering the protein or peptide from the cell and/or the culture medium.

18. A method of obtaining a yeast cell that produces a desired protein or peptide comprising the steps of:
(a) transforming a yeast cell having a genome which comprises at least two DNA domains suitable for integration of one or more copies of a desired gene, comprise diploid loci or multiple copies of a single locus and are non-ribosomal RNA encoding DNA domains, with a DNA molecule comprising a desired gene which codes for the said protein or peptide, or a precursor thereof, and a all or a portion of said domain;
(b) selecting or screening for cells having obtained at least one copy of the said desired gene integrated into at least one of said non-ribosomal RNA encoding DNA domains suitable for integration of one or more copies of a desired gene;
(c) propagating the cells obtained in (b) and screening or selecting for cells having obtained at least one copy of the said desired gene integrated into at least two of said non-ribosomal RNA encoding DNA domains.

19. The method of claim 18 comprising in addition to step (a), (b) and (c) the step of:
(d) propagating the cells obtained in (c) and screening or selecting for cells having obtained at least one copy of the said desired gene integrated into an additional copy of said non-ribosomal RNA encoding DNA domains.

20. The method of claim 19 comprising in addition to step (a), (b) (c) and (d) the step of:
(e) repeating step (d) until each copy of said non-ribosomal RNA encoding DNA domains has obtained at least one integrated copy of the said desired gene.

21. The method of claim 18 wherein, a bidirectional selectable marker is used in the transformation of the yeast cells in step (a), and wherein removal of the selectable marker is effected prior to step (c).

22. A method of claim 18 wherein the yeast cell is a Kluyveromyces cell.

23. The method of claim 20 wherein the yeast cell is a Kluyveromyces cell.

24. The method of claim 21, wherein the bi-directional selectable marker is a dominant marker.

25. The method of claim 21, wherein subsequent to the removal of the bi-directional selectable marker, step (a) is repeated at least once.

26. The method of claim 24, wherein the selectable marker gene is an acetamidase gene.

27. A method of obtaining a yeast cell that produces a desired protein or peptide comprising the steps of:
a) transforming a yeast cell having a genome which comprises at least two DNA domains suitable for integration of one or more copies of a desired gene, which domains comprise diploid loci or multiple copies of a single locus and are non-ribosomal RNA encoding DNA domains, with a DNA molecule comprising a desired gene which codes for the said protein or peptide, or a precursor thereof, and all or a portion of said domain;
b) selecting or screening for cells having obtained at least one copy of the said desired gene integrated into at least one of said non-ribosomal RNA encoding DNA domains suitable for integration of, one or more copies of a desired gene;
c) transforming at cell obtained in (b) with a second DNA molecule comprising a selectable marker gene, and all or a portion of said domain;
d) selecting or screening for cells having obtained at least one copy of the said selectable marker gene integrated into one of said nonribosomal RNA encoding DNA domains without one or more copies of the desired gene;
e) propagating the cells obtained in (d) and screening or selecting for cells having lost the selectable marker gene and having obtained at least one copy of the said desired gene integrated into at least two of said non-ribosomal RNA encoding DNA domains.

28. The method of claim 27, wherein the selectable marker gene is a bidirectional marker gene.

29. The method of claim 27, wherein the selectable marker gene is a dominant bi-directional marker gene.

30. The method of claim 27 wherein the yeast cell is a Kluyveromyces cell.

31. The method of claim 28, wherein the selectable marker gene is an acetamidase gene.

32. A method of obtaining a yeast cell that produces a desired protein or peptide, wherein said method comprises the steps of:
a) obtaining a transformed yeast cell comprising at least two DNA domains each suitable for integration of one or more copies of said desired gene, which domains comprise diploid loci or multiple copies of a single locus, and at least one copy of a desired gene integrated in a first DNA domain, wherein the desired gene is flanked by direct repeats;

b) isolating single colonies from the progeny of the cell obtained in (a);

c) screening for single colony isolates having cells which have obtained at least one additional tandemly integrated copy of the desired gene in at least one DNA domain other than the first DNA domain and, optionally;

d) repeating steps (a) to (c) on the cells obtained in (c) until a desired achievable number equal to or greater than two of tandemly repeated copies of the desired gene is obtained.

33. The method of claim 32, wherein the transformed yeast cell is a yeast cell having a genome which comprises at least two DNA domains suitable for integration of one or more copies of a desired gene, which domains comprise diploid loci or multiple copies of a single locus and are non-ribosomal RNA encoding DNA domains, and wherein the desired gene is integrated into at least one copy of said DNA domain, and wherein the method further comprises the steps of:

e) propagating the cells obtained in (c) or (d) and screening or selecting for cells having obtained copies of said desired gene integrated into at least two of said non-ribosomal RNA encoding DNA domains, and, optionally;

f) repeating the propagation and screening or selecting of (e) on the cells obtained in (e) until a desired achievable number of said non-ribosomal RNA encoding DNA domains equal to or greater than two have obtained integrated copies of said desired gene.

34. The method of claim 32 wherein the yeast cell is a Kluyveromyces cell.

35. The method of claim 33 wherein the yeast cell is a Kluyveromyces cell.

36. A yeast cell of the genus Kluyveromyces which is non-haploid for at least one locus, and which yeast cell has in each allele of the said non-haploid locus one or more copies of a desired gene integrated.

37. The Kluyveromyces cell of claim 36, which has the same number of copies of the said desired gene integrated in each allele.

38. The yeast cell of claim 36, which yeast cell is a selectable marker gene free yeast cell.

39. A method for making a protein, a peptide or a metabolite in yeast cells, by growing the yeast cells under conditions giving rise to the production of said protein, peptide or metabolite, wherein the yeast cell is a yeast cell according to claim 36.

40. The Kluyveromyces cell of claim 37, wherein the desired gene is a non-yeast gene.

41. A method for making a protein, a peptide or a metabolite in yeast cells, by growing the yeast cells under conditions giving rise to the production of said protein, peptide or metabolite, wherein the yeast cell is a yeast cell according to claim 40.

42. A Kluyveromyces yeast cell having at least 3 copies of a gene encoding lactase, or a mutant thereof, incorporated into at least two substantially homologous non-ribosomal RNA encoding DNA domains in its chromosomal genome.

43. A method for making lactase, characterised by propagating the cells of claim 42 under conditions conducive to the production of lactase, or a mutant thereof, and optionally recovering the said lactase from the cells.

44. Kluyveromyces yeast cell having at least 3 copies of a gene encoding chymosin, or a precursor or a mutant thereof, incorporated into at least two substantially homologous non-ribosomal RNA encoding DNA domains in its chromosomal genome.

45. A method for making chymosin, or a precursor thereof, characterised by propagating the cells of claim 44 under conditions conducive to the production of chymosin, or a precursor or a mutant thereof, and optionally recovering the chymosin, or a precursor or mutant thereof, from the cells and/or the culture medium.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial
      Sequence:oligonucleotide, PCR primer AB 5677

<400> SEQUENCE: 1
cattgctgtt ttacttgaga tttc                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial
      Sequence:oligonucleotide, PCR primer AB 5678

<400> SEQUENCE: 2
aattggttta ccgtacttcc agtc                                            24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial
      Sequence:oligonucleotide, PCR primer LACP1 (also
      designated P1)

<400> SEQUENCE: 3

```
atctatctgt tcctttcctt                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial
      Sequence:oligonucleotide, PCR primer LACT1 (also
      designated T1)

<400> SEQUENCE: 4
gtatgtactt acaggtatat                                               20

<210> SEQ ID NO 5
<211> LENGTH: 40
<212> TYPE: DNA
<213> ORGANISM: Artificial Sequence
<220> FEATURE:
<223> OTHER INFORMATION: Description of Artificial
      Sequence:oligonucleotide, PCR primer 4596

<400> SEQUENCE: 5
ttctcttata gtcgactcta attcttctaa gcttctaccc                         40

<210> SEQ ID NO 6
<211> LENGTH: 23
<212> TYPE: DNA
<213> ORGANISM: Artificial Sequence
<220> FEATURE:
<223> OTHER INFORMATION: Description of Artificial
      Sequence:oligonucleotide, PCR primer 4597

<400> SEQUENCE: 6
ttcctttggt tactagtatc gtc                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial
      Sequence:oligonucleotide, PCR primer 4719

<400> SEQUENCE: 7
ccaatgcaat ccatgtactc aac                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial
      Sequence:oligonucleotide, PCR primer 4720

<400> SEQUENCE: 8
taattctgca tcgatccagt atg                                           23
```